United States Patent [19]
Roberts et al.

[11] Patent Number: 5,444,071
[45] Date of Patent: * Aug. 22, 1995

[54] QUINOLINE DERIVATIVES AND USE THEREOF AS ANGIOTENSIN II ANTAGONISTS

[75] Inventors: David A. Roberts, Congleton; Simon T. Russell, Macclesfield; Robert J. Pearce, Wilmslow, all of England

[73] Assignee: Imperial Chemical Industries PLC, England

[ * ] Notice: The portion of the term of this patent subsequent to Nov. 29, 2011 has been disclaimed.

[21] Appl. No.: 58,825

[22] Filed: May 4, 1993

Related U.S. Application Data

[63] Continuation of Ser. No. 565,764, Aug. 10, 1990, abandoned.

[30] Foreign Application Priority Data

Aug. 11, 1989 [GB] United Kingdom ................. 8918402
Feb. 13, 1990 [GB] United Kingdom ................. 9003187

[51] Int. Cl.$^6$ .................. A61K 31/47; C07D 215/233
[52] U.S. Cl. .................... 514/312; 514/290; 546/4; 546/10; 546/110; 546/153; 546/155; 546/156; 546/157
[58] Field of Search ................. 514/290, 312; 546/10, 546/4, 110, 153, 155, 156, 157

[56] References Cited

U.S. PATENT DOCUMENTS

| | | | |
|---|---|---|---|
| 4,576,953 | 3/1986 | Le Count | 514/312 |
| 4,607,040 | 8/1986 | Pearce et al. | 514/312 |
| 4,820,843 | 4/1989 | Aldrich et al. | 548/252 |
| 4,880,804 | 11/1989 | Carini et al. | 546/199 |
| 4,920,131 | 4/1990 | Huang et al. | 514/311 |
| 5,028,615 | 7/1991 | Huang et al. | 546/180 |
| 5,219,863 | 7/1993 | Roberts et al. | 514/312 |
| 5,227,387 | 7/1993 | Dreikorn et al. | 514/312 |
| 5,240,940 | 8/1993 | Arnold et al. | 514/312 |
| 5,246,944 | 9/1993 | Greenlee et al. | 514/312 |
| 5,296,484 | 3/1994 | Coghlan et al. | 514/312 |

FOREIGN PATENT DOCUMENTS

| | | |
|---|---|---|
| 0253310 | 1/1988 | European Pat. Off. . |
| 0315399 | 5/1989 | European Pat. Off. . |
| 0323841 | 7/1989 | European Pat. Off. . |
| 0326328 | 8/1989 | European Pat. Off. . |
| WO89/04304 | 5/1989 | WIPO . |

OTHER PUBLICATIONS

Youssefyeh, R. D., et al. (principal author Huang) *J. Med. Chem.* (1990), 33, 1186–1194.
*Chem. Abstr.* (1990), 112, 17, Abstract 131,890u.
Huang, F-C *J. Med. Chem.* (1990), 33, 1194–1200.
*J. Chem. Soc., Perkin Trans.* 1, (14), 1803–8, (1972) by Proctor et al.
M. I. Husain, et al., *J. Chem. Soc. Pak.* (1986) 8(3), 335–9.

*Primary Examiner*—Yogendra N. Gupta
*Attorney, Agent, or Firm*—Cushman Darby & Cushman

[57] ABSTRACT

The invention concerns pharmaceutically useful novel compounds of the formula I, in which $R^1$, $R^2$, $R^3$, $R^4$, $R^5$, Ra, A, X and Z have the various meanings defined herein, and their non-toxic salts, and pharmaceutical compositions containing them. The novel compounds are of value in treating conditions such as hypertension and congestive heart failure. The invention further concerns processes for the manufacture of the novel compounds and the use of the compounds in medical treatment.

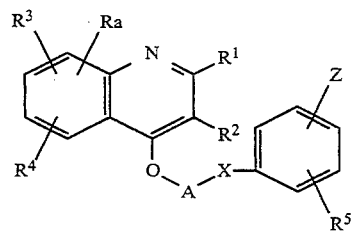

22 Claims, No Drawings

QUINOLINE DERIVATIVES AND USE THEREOF AS ANGIOTENSIN II ANTAGONISTS

This is a continuation of application Ser. No. 07/565,764 filed on Aug. 10, 1990 now abandoned.

This invention concerns novel nitrogen compounds and, more particularly, novel quinoline derivatives which possess pharmacologically useful properties in antagonising at least in part one or more of the actions of the substances known as angiotensins, and in particular of that known as angiotensin II (hereinafter referred to as "AII"). The invention also concerns pharmaceutical compositions of the novel compounds for use in treating diseases or medical conditions such as hypertension, congestive heart failure and/or hyperaldosteronism in warm-blooded animals (including man), as well as in other diseases or medical conditions in which the renin-angiotensin-aldosterone system plays a significant causative role. The invention also includes processes for the manufacture of the novel compounds and their use in treating one of the afore-mentioned diseases or medical conditions and for the production of novel pharmaceuticals for use in such medical treatments.

The angiotensins are key mediators of the renin-angiotensin-aldosterone system, which is involved in the control of homeostasis and fluid/electrolyte balance in many warm-blooded animals, including man. The angiotensin known as AII is produced by the action of angiotensin converting enzyme (ACE) from angiotensin I, itself produced by the action of the enzyme renin from the blood plasma protein angiotensinogen. AII is a potent spasmogen especially in the vasculature and is known to increase vascular resistance and blood pressure. In addition, the angiotensins are known to stimulate the release of aldosterone and hence result in vascular congestion and hypertension via sodium and fluid retention mechanisms. Hitherto there have been a number of different approaches to pharmacological intervention in the renin-angiotensin-aldosterone system for therapeutic control of blood pressure and/or fluid/electrolyte balance, including, for example, inhibiting the actions of renin or ACE. However, there remains a continuing need for an alternative approach because of the side-effects and/or idiosyncratic reactions associated with any particular therapeutic approach.

Certain substituted imidazoles and benzimidazoles described in European Patent Application, publication no. 253310 A2 and U.S. Pat. No. 4,880,804 respectively are known to inhibit the action of angiotensin II, as too are certain substituted pyrroles, pyrazoles and triazoles described in European Patent Application, publication no. 323841A2. Also certain structurally related quinoline derivatives described in European Patent Application, publication no. 348155 A1 are known to be antagonists of leukotriene D4. In addition, a structurally related compound, methyl 2-[(3-methoxycarbonylquinolin-4-yloxy)methyl]benzoate, is described in *J. Chem. Soc., Perkin Trans.* 1, 1972, 1803-8 but without indication of any useful pharmacological properties.

We have now discovered that the compounds of the invention (set out below) surprisingly antagonise one or more of the actions of the substances known as angiotensins (and in particular of AII) and thus minimise the physiological effects associated with their presence in warm-blooded animals (including man) and this is the basis of the invention.

According to the invention there is provided a quinoline derivative of the formula I (set out hereinafter, together with the other chemical formulae identified by Roman numerals) wherein $R^1$ is hydrogen, (1-8C)alkyl, (3-8C)cycloalkyl, phenyl or substituted (1-4C)alkyl, the latter containing one or more fluoro substituents or bearing a (3-8C)cycloalkyl, hydroxy, (1-4C)alkoxy or phenyl substituent; $R^2$ is hydrogen, (1-8C)alkyl, (3-8C)cycloalkyl, (3-8C)cycloalkyl-(1-4C)alkyl, carboxy, (1-4C)alkoxycarbonyl, cyano, nitro, phenyl or phenyl(-1-4C)alkyl; $R^3$ and $R^4$ are independently selected from hydrogen, (1-4C)alkyl, (1-4C)alkoxy, fluoro(1-4C)alkoxy, halogeno, hydroxy, trifluoromethyl, cyano, nitro, amino, (1-4C)alkanoylamino, alkylamino and dialkylamino of up to 6 carbon atoms, dialkylamino-alkyl of 3 to 8 carbon atoms, (1-4C)alkanoyl, carbamoyl, N-alkylcarbamoyl and di-(N-alkyl)carbamoyl of up to 7 carbon atoms, carboxy, (1-4C)alkoxycarbonyl, (1-6C)alkylthio, (1-6C)alkylsulphinyl, (1-6C)alkylsulphonyl, and substituted (1-4C)alkyl, the latter bearing an amino, hydroxy or (1-4C)alkoxy substituent; or $R^3$ and $R^4$ together form (1-4C)alkylenedioxy attached to adjacent carbon atoms of the benzene moiety of formula I; Ra and $R^5$ are independently selected from hydrogen, (1-4C)alkyl, (1-4C)alkoxy, halogeno, trifluoromethyl, cyano and nitro; A is methylene; X is phenylene optionally bearing a substituent selected from (1-4C)alkyl, (1-4C)alkoxy, halogeno, trifluoromethyl, cyano and nitro, or X is a direct bond between the adjacent phenyl group and moiety A; Z is 1H-tetrazol-5-yl, —CO.NH.(1H-tetrazol-5-yl) or a group of the formula —CO.OR$^6$ or —CO.NH.SO$_2$.R$^7$ in which R$^6$ is hydrogen or a non-toxic, biodegradable residue of a physiologically acceptable alcohol or phenol, and R$^7$ is (1-6C)alkyl, (3-8C)cycloalkyl or phenyl; and wherein any of said phenyl moieties may be unsubstituted or bear one or two substituents independently selected from (1-4C)alkyl, (1-4C)alkoxy, halogeno, cyano and trifluoromethyl; or a non-toxic salt thereof; but excluding methyl 2-[(3-methoxycarbonylquinolin-4-yloxy)methyl]benzoate.

It will appreciated that, depending on the nature of the substituents, certain of the formula I compounds may possess one or more chiral centres and may be isolated in one or more racemic or optically active forms. It is to be understood that this invention concerns any form of such a compound of formula I which possesses the afore-mentioned useful pharmacological properties, it being well known how to make optically active forms, for example by synthesis from suitable chiral intermediates, and how to determine their pharmacological properties, for example by use of the standard tests described hereinafter.

It is to be understood that generic terms such as "alkyl" include both straight and branched chain variants when the carbon numbers permit. However, when a particular radical such as "propyl" is given, it is specific to the straight chain variant, branched chain variants such as "isopropyl" being specifically named where intended. The same convention applies to other radicals.

A particular value for $R^1$ or $R^2$ when it is alkyl is, for example, methyl, ethyl, propyl, butyl, isobutyl, sec-butyl, pentyl or hexyl; and when it is cycloalkyl is, for example, cyclopropyl, cyclopentyl or cyclohexyl.

A particular value for $R^1$ when it is alkyl bearing one or more fluoro substituents is, for example, fluoromethyl, trifluoromethyl, 2,2,2-trifluoroethyl or pentafluoroethyl; and when it is alkyl bearing a hydroxy, cycloalkyl, (1–4C)alkoxy or phenyl substituent is, for example, hydroxymethyl, 1-hydroxyethyl, 2-hydroxyethyl, cyclopropylmethyl, cyclopentylmethyl, cyclohexylmethyl, 2-methoxyethyl, 2-ethoxyethyl, benzyl, 1-phenylethyl or 2-phenylethyl.

A particular value for $R^2$ when it is cycloalkyl-alkyl is, for example, cyclopropylmethyl, cyclopentylmethyl, cyclohexylmethyl or 2-cyclopentyl-ethyl; when it is phenylalkyl is, for example, benzyl, 1-phenylethyl or 2-phenylethyl; and when it is alkoxycarbonyl is, for example, methoxycarbonyl, ethoxycarbonyl or propoxycarbonyl.

Appropriate values for $R^3$, $R^4$, $R^5$ or Ra, or for an optional substituent which may be present when X is phenylene, as defined above, include by way of example:—
for alkyl: methyl and ethyl; for alkoxy: methoxy and ethoxy; for fluoroalkoxy: trifluoromethoxy, 2-fluoroethoxy, 2,2,2-trifluoroethoxy and 3,3,3-trifluoropropoxy; for halogeno: fluoro, chloro, bromo and iodo; for alkanoylamino: formamido, acetamido and propanamido; for alkylamino: methylamino, ethylamino and butylamino; for dialkylamino: dimethylamino, diethylamino and dipropylamino; for dialkylamino-alkyl: dimethylaminomethyl, 2-(dimethylamino)ethyl, 2-(diethylamino)ethyl and 3-(diethylamino)propyl; for alkanoyl: formyl, acetyl and butyryl; for N-alkylcarbamoyl: N-methyl and N-ethylcarbamoyl; for di(N-alkyl)carbamoyl: N,N-dimethylcarbamoyl and N,N-diethylcarbamoyl; for alkoxycarbonyl: methoxycarbonyl, ethoxycarbonyl and propoxycarbonyl; for alkylthio: methylthio, ethylthio and butylthio; for alkylsulphinyl: methylsulphinyl, ethylsulphinyl and butylsulphinyl; and for alkylsulphonyl: methylsulphonyl, ethylsulphonyl and butylsulphonyl; for alkyl bearing an amino, hydroxy or alkoxy substituent: hydroxymethyl, 1-hydroxyethyl, 2-hydroxyethyl, aminomethyl, 2-aminoethyl, 2-methoxyethyl and 2-ethoxyethyl; and alkylenedioxy: methylenedioxy and ethylenedioxy.

A particular value for $R^6$ when it is a non-toxic, biodegradable residue of a physiologically acceptable alcohol or phenol is, for example, a residue derived from a (1–6C)alkanol such as methanol or ethanol, or phenol, glycerol or the like.

A particular value for $R^7$ when it is alkyl is, for example, methyl, ethyl, propyl, isopropyl, butyl or pentyl; and when it is cycloalkyl is, for example, cyclobutyl, cyclopentyl or cyclohexyl.

Particular values for optional substituents which may be present on one or more phenyl moieties include, by way of example, for halogeno: fluoro, chloro and bromo; for alkyl: methyl and ethyl; and for alkoxy: methoxy and ethoxy.

A specific value for X which is of particular interest is, for example, p-phenylene.

A preferred value for $R^6$ or $R^5$ is, for example, hydrogen and for $R^1$ is, for example, methyl, ethyl or propyl.

A preferred value for A is, for example, when it is methylene.

A preferred group of compounds of the invention comprises those compounds of the formula Ia (set out hereinafter) wherein $R^1$, $R^2$, $R^3$, $R^4$ and $R^5$ have any of their meanings as defined above and $Z^1$ is carboxy, 1H-tetrazol-5-yl or benzenesulphonamido, the latter optionally containing one or two substituents independently selected from halogeno (such as fluoro, chloro or bromo), (1–4C)alkyl (such as methyl or ethyl), (1–4C)alkoxy (such as methoxy or ethoxy), cyano, nitro and trifluoromethyl; together with the non-toxic salts thereof.

A preferred value for Z or $Z^1$ is, for example, carboxy or 1H-tetrazol-5-yl, which latter is especially preferred and, in particular, when it is attached ortho to the group X.

A particularly preferred combination of values in any of the above definitions is wherein the quinoline moiety together with the attached substituents $R^1$, $R^2$, $R^3$ and $R^4$, and Ra when present, has any of the following values:—2-methylquinoline, 2-ethylquinoline, 2-ethyl-6-methoxyquinoline, 6,7-dimethoxy-2-ethylquinoline, 2-ethyl-5,6,7-trimethoxyquinoline, 2-ethyl-6-hydroxyquinoline, 2-ethyl-6-methylthioquinoline, 2-ethyl-7-hydroxymethylquinoline, 2-ethyl-6-(2-fluoroethoxy)-quinoline, 2-ethyl-6-(2,2,2-trifluoroethoxy)quinoline, 2-ethyl-6-carboxamidoquinoline, 2-ethyl-6-fluoroquinoline, 2-ethyl-6-isopropoxyquinoline or 6-aminomethyl-2-ethylquinoline; and in which the substituent O.A.X- is attached at the 4-position of the quinoline ring.

Compounds of the invention which are of particular interest include, for example, the specific embodiments set out hereinafter in the accompanying Examples. Of these compounds, those described in Examples 7, 25, 33, 36, 38 and 47 are particularly preferred and are provided, together with their non-toxic salts, as a further feature of the invention.

Although all of the formula I compounds can form salts with suitable acids, it will be appreciated that those compounds of formula I wherein Z is other than an ester group or in which $R^3$ or $R^4$ is a carboxy group can form salts with bases as well as with acids. Particularly suitable non-toxic salts for such compounds therefore also include, for example, salts with bases affording physiologically acceptable cations, for example, alkali metal (such as sodium and potassium), alkaline earth metal (such as magnesium and calcium), aluminium and ammonium salts, as well as salts with suitable organic bases, such as with ethanolamine, methylamine, diethylamine or triethylamine, as well as salts with acids forming physiologically acceptable anions, such as salts with mineral acids, for example with hydrogen halides (such as hydrogen chloride and hydrogen bromide), sulphuric and phosphoric acid, and with strong organic acids, for example with p-toluenesulphonic and methanesulphonic acids.

The compounds of formula I may be obtained by standard procedures of organic chemistry well known in the art for the production of structurally analogous compounds. Such procedures are provided as a further feature of the invention and include, by way of example, the following procedures in which the generic radicals have any of the values given above, unless stated otherwise:

a) For those compounds in which Z is carboxy (that is in which Z is a group of the formula —CO.OR$^6$ in which $R^6$ is hydrogen), a carboxylic acid derivative of the formula II, in which Q is a protected carboxy group selected from (1–6C)alkoxycarbonyl (especially methoxy-, ethoxy-, propoxy- or t-butoxy-carbonyl), phenoxycarbonyl, benzyloxycarbonyl and carbamoyl, is converted to carboxy.

The conversion may be carried out, for example by hydrolysis, conveniently in the presence of a suitable base such as an alkali metal hydroxide, for example, lithium, sodium or potassium hydroxide. The hydrolysis is generally carried out in the presence of a suitable aqueous solvent or diluent, for example in an aqueous (1–4C)alkanol, such as aqueous methanol or ethanol. However, it may also be performed in a mixture of an aqueous and non-aqueous solvent such as water and toluene using a conventional quaternary ammonium phase tranfer catalyst. The hydrolysis is generally performed at a temperature in the range, for example, 0°–120° C., depending on the reactivity of the group Q. In general, when Q is carbamoyl, temperatures in the range, for example, 40°–120° C. are required to effect the hydrolysis.

Alternatively, when Q is benzyloxycarbonyl, the conversion may also be performed by hydrogenolysis, for example using hydrogen at 1–3 bar in the presence of a suitable catalyst, such as palladium on charcoal or on calcium sulphate, in a suitable solvent or diluent such as a (1–4C)alkanol (typically ethanol or 2-propanol) and at a temperature in the range, for example, 0°–40° C.

Further, when Q is t-butoxycarbonyl, the conversion may also be carried out by hydrolysis at a temperature in the range, for example, 0°–100° C., in the presence of a strong acid catalyst, such as trifluoroacetic acid. The hydrolysis may either be performed in an excess of the acid or in the presence of a suitable diluent such as tetrahydrofuran, t-butyl methyl ether or 1,2-dimethoxyethane.

b) For those compounds of formula I wherein Z is tetrazolyl, a compound of the formula III in which L is a suitable protecting group, such as trityl, benzhydryl, trialkyltin (for example tributyltin) or triphenyltin, affixed to a nitrogen of the tetrazolyl moiety, is deprotected.

The reaction conditions used to carry out the deprotection necessarily depend on the nature of the group L. As an illustration, when it is trityl, benzhydryl, trialkyltin or triphenyltin, the decomposition conditions include, for example, acid catalysed hydrolysis in a mineral acid (such as aqueous hydrochloric acid), conveniently in an aqueous solvent (such as aqueous dioxan or 2-propanol). Alternatively, a trityl or benzhydryl group may be removed by hydrogenolysis, for example as described in (a) above for conversion of a benzyloxycarbonyl to a carboxy.

Compounds of the formula III wherein L is trialkyltin or triphenyltin may be obtained, for example, by reaction of a compound of formula II wherein Q is cyano with a trialkyltin azide, such as tributyltin azide, or triphenyltin azide respectively. The reaction is conveniently carried out in a suitable solvent or diluent, such as toluene or xylene, and at a temperature in the range, for example, 50°–150° C. Compounds of the formula II wherein Q is cyano may be obtained by bromination of a suitably substituted 4'-methylbiphenylcarbonitrile to the corresponding bromomethyl derivative followed by alkylation of a quinolone of formula IV in a similar manner to that described in process (c) described hereinafter.

c) A quinolone of the formula IV wherein $R^1$ is other than hydrogen is alkylated with a compound of the formula V wherein Hal. stands for a suitable leaving group such as chloro, bromo, iodo, methanesulphonyloxy or p-toluenesulphonyloxy.

The reaction is generally carried out in the presence of a suitable base, for example, an alkali metal alkoxide such as sodium methoxide or sodium ethoxide or an alkali metal hydride such as sodium hydride or an organic base such as diisopropylethylamine and in a suitable solvent or diluent, for example, a (1–4C)alkanol such as methanol or ethanol when an alkali metal alkoxide is used, or in a polar solvent such as N,N-dimethylformamide and at a temperature in the range, for example, 10°–100° C. Alternatively, a quaternary ammonium hydroxide may be used in a mixture of an aqueous and non-aqueous solvent such as water and dichloromethane. In carrying out process (c), when in the starting material Z is an acidic group, about two molecular equivalents of a suitable base is generally required, whereas when Z is a non-acidic group the presence of one molecular equivalent of a suitable base is generally sufficient.

Procedure (c) is particularly suitable for the production of those compounds of the formula I in which Z is a group of the formula —CO.$OR^6$ in which $R^6$ is other than hydrogen, for example wherein $R^6$ is (1–6C)alkyl, benzyl or phenyl, which compounds are also starting materials of formula II for the reaction described in (a) above. Similarly, using an analogous procedure, but starting with the appropriate halomethyl tetrazolyl derivative of the formula VI, the starting materials of the formula III may be obtained for procedure (b).

The majority of the quinolones of formula IV are already known and the remainder can be made by analogy therewith using standard procedures of organic chemistry well known in the art, for example as described in standard works of heterocyclic chemistry such as that edited by Elderfield. The necessary compounds of the formula V (and also of formula VI) may be made by standard procedures such as those which are illustrated in Scheme 1 for compounds in which X is phenylene. Compounds of the formula VI wherein X is phenylene may also be conveniently obtained by reaction of a Grignard reagent, formed from a suitably substituted 4-bromotoluene, with a trialkyltin halide, such as tributyltin chloride, followed by reaction of the resulting (substituted)phenyltrialkyltin compound with a bromobenzonitrile in the presence of a palladium(O) catalyst, such as tetrakis(triphenylphosphine)palladium, and azo(bisisobutyronitrile). The resultant substituted 4'-methyl-biphenylcarbonitrile may then be converted to a compound of the formula VI by carrying out steps (b), (c) and (d) in a similar manner to that shown in Scheme 1. Alternatively, suitably substituted 4'-methyl-biphenylcarbonitriles may be obtained by reaction of 4-methylphenylboronic acid with an appropriately substituted bromobenzonitrile in the presence of a suitable palladium catalyst, such as palladium (II)chloride or tetrakis(triphenylphosphine)palladium, and azo(bisisobutyronitrile).

d) A halogenoquinoline of the formula VII wherein $Y^1$ is a halogeno group (such as chloro, bromo or iodo) is reacted with an alcohol of the formula VIII.

The reaction is generally carried out in the presence of a suitable base, for example an alkali metal alkoxide such as sodium methoxide or ethoxide or an alkali metal hydride such as sodium hydride and in a suitable solvent or diluent, for example a (1–4C)alkanol such as methanol or ethanol when an alkali metal alkoxide is used, or a polar solvent such as N,N-dimethylformamide. Alternatively, an alcohol of the formula VIII may be used in the form of its preformed alkali metal salt (when Z is a non-acidic group) or di-alkali metal salt (when Z is an acidic group). The reaction is usually performed at a temperature in the range of 40° to 120° C. Alternatively, the reaction may in preference be carried out with a formula VIII compound in the presence of an acid catalyst such as p-toluenesulphonic acid, instead of under basic conditions, and in the presence of an inert solvent or diluent such as toluene.

The haloquinolines of the formula VII may be obtained, for example, by halogenation of the corresponding quinolones of formula IV, for example, by reaction with phosphorus oxychloride in the absence of a solvent, or in the presence of an inert solvent or diluent such as toluene or dioxane, and at a temperature in the range 60° to 110° C. The alcohols of the formula VIII are in general known or can be prepared by standard procedures well known in the art.

Whereafter, those compounds of formula I wherein Z is 1H-tetrazol-5-yl may be obtained by stepwise conversion of a compound of the formula I wherein Z is a group of the formula —CO.OR$^6$ into the corresponding nitrile under standard conditions, followed by reaction of the nitrile with an azide such as an alkali metal azide, preferably in the presence of an ammonium halide, and preferably in the presence of a suitable polar solvent such as N,N-dimethylformamide and at a temperature in the range, for example, 50° to 160° C.

Whereafter, those compounds of the formula I wherein Z is —CO.NH.(1H-tetrazol-5-yl) a group of the formula —CO.NH.SO$_2$R$^7$ or a group of the formula —CO.OR$^6$ in which R$^6$ is other than hydrogen, may be obtained, for example, by reacting a carboxylic acid of the formula I in which Z is carboxy (or a reactive derivative of said acid) with 5-aminotetrazole a sulphonamide of the formula NH$_2$.SO$_2$R$^7$ or a salt thereof (for example, an alkali metal salt), or a hydroxy compound of the formula HO.R$^6$ or with a salt thereof (for example, an alkali metal thereof). Suitable reactive derivatives include, for example the chloride, bromide, azide, anhydride and mixed anhydride with formic or acetic acid of the carboxylic acid of formula I as defined above. When the free acid form is used, the reaction is generally carried out in the presence of a suitable dehydrating agent such as dicyclohexycarbodiimide or 3-(3-dimethylaminopropyl)-1-ethylcarbodiimide in the presence of a base such as triethylamine or pyridine. When a reactive derivative is used, either the reaction is carried out in the presence of a base such as mentioned above, or, for the preparation of a compound of the formula I wherein Z is a group of the formula —CO.NH.SO$_2$R$^7$ or a group of the formula —CO.OR$^6$ the sulphonamide or hydroxy compound is used in the form of a salt, such as its alkali metal salt (in particular the lithium, sodium or potassium salt thereof). The reaction is generally performed in the presence of a suitable diluent or solvent such as dioxan, t-butyl methyl ether or tetrahydrofuran and at a temperature in the range, for example, 0°–60° C.

Whereafter, when a non-toxic salt of a compound of formula I is required, it may be obtained, for example, by reaction with the appropriate base affording a physiologically acceptable cation, or with the appropriate acid affording a physiologically acceptable anion, or by any other conventional salt formation procedure.

Further, when an optically active form of a compound of formula I is required, one of the aforesaid processes may be carried out using an optically active starting material. Alternatively, the racemic form of a compound of formula I in which Z is an acidic group may be resolved, for example by reaction with an optically active form of a suitable organic base, for example, ephedrine, N,N,N-trimethyl-(1-phenylethyl)ammonium hydroxide or 1-phenylethylamine, followed by conventional separation of the diastereoisomeric mixture of salts thus obtained, for example by fractional crystallisation from a suitable solvent, for example a (1–4C)alkanol, whereafter the optically active form of said compound of formula I may be liberated by treatment with acid using a conventional procedure, for example using an aqueous mineral acid such as dilute hydrochloric acid.

Certain of the intermediates defined herein are novel, for example the compounds of the formula II, III and IV, and are provided as a further feature of the invention.

As stated above, the compounds of formula I will have beneficial pharmacological effects in warm-blooded animals (including man) in diseases and medical conditions where amelioration of the vasoconstrictor and fluid retaining properties of the renin-angiotensin-aldosterone system is desirable, at least in part by antagonism of one or more of the physiological actions of AII. The compounds of the invention will thus be useful in the treatment of diseases or medical conditions such as hypertension, congestive heart failure and/or hyperaldosteronism in warm-blooded animals (including man), as well as in other diseases or medical conditions in which the renin-angiotensin-aldosterone system plays a significant causative role.

The antagonism of one or more of the physiological actions of AII and, in particular, the antagonism of the interaction of AII with the receptors which mediate its effects on a target tissue, may be assessed using one or more of the following, routine laboratory procedures:

Test A: This in vitro procedure involves the incubation of the test compound initially at a concentration of 100 micromolar (or less) in a buffered mixture containing fixed concentrations of radiolabelled AII and a cell surface membrane fraction prepared from a suitable angiotensin target tissue. In this test, the source of cell surface membranes is the guinea pig adrenal gland which is well known to respond to AII. Interaction of the radiolabelled AII with its receptors (assessed as radiolabel bound to the particulate membrane fraction following removal of unbound radiolabel by a rapid filtration procedure such as is standard in such studies) is antagonized by compounds which also bind to the membrane receptor sites and the degree of antagonism (observed in the test as displacement of membrane-bound radioactivity) is determined readily by comparing the receptor-bound radioactivity in the presence of the test compound at the specified test concentration with a control value determined in the absence of the test compound. Using this procedure compounds showing at least 50% displacement of radiolabelled AII binding at a concentration of $10^{-4}$M are retested at lower concentrations to determine their potency. For determination of the IC$_{50}$ (concentration for 50% displacement of radiolabelled AII binding), concentrations of the test compound are ordinarily chosen to allow testing over at least four orders of magnitude centred about the predicted approximate IC$_{50}$, which latter is subsequently determined from a plot of percentage displacement against concentration of the test compound.

In general, compounds of formula I as defined above wherein Z is an acidic group show significant inhibition in Test A at a concentration of 50 micromolar or much less.

Test B: This in vitro test involves the measurement of the antagonistic effects of the test compound against AII-induced contractions of isolated rabbit aorta, maintained in a physiological salt solution at 37° C. In order to ensure that the effect of the compound is specific to antagonism of AII, the effect of the test compound on noradrenaline-induced contractions may also be determined in the same preparation.

In general, compounds of formula I as defined above wherein Z is an acidic group show significant inhibition in Test B at a final concentration of 50 micromolar or much less. [Note: Compounds of formula I wherein Z is a group of the formula —CO.OR$^6$ in which R$^6$ is other than hydrogen in general show only weak activity in the in vitro Tests A or B.]

Test C: This in vivo test involves using terminally-anaesthetised or conscious rats in which an arterial catheter has been implanted under anaesthesia for the measurement of changes in blood pressure. The AII antagonistic effects of the test compound following oral or parenteral administration, are assessed against angiotensin II-induced pressor responses. To ensure that the effect is specific, the effect of the test compound on vasopressin-induced pressor responses may also be determined in the same preparation.

The compounds of formula I generally show specific AII-antagonist properties in Test C at a dose of 50 mg/kg body weight or much less, without any overt toxicological or other untoward pharmacological effect.

Test D: This in vivo test involves the stimulation of endogenous AII biosynthesis in a variety of species including rat, marmoset and dog by introducing a diet of low sodium content and giving appropriate daily doses of a saluretic known as frusemide. The test compound is then administered orally or parenterally to the animal in which an arterial catheter has been implanted under anaesthesia for the measurement of changes in blood pressure.

In general compounds of formula I will show AII-antagonist properties in Test D as demonstrated by a significant reduction in blood pressure at a dose of 50 mg/kg body weight or much less, without any overt toxicological or other untoward pharmacological effect.

By way of illustration of the angiotensin II inhibitory properties of compounds of formula I, the compound of example 7 gave the following results in tests A, B and C described above:—

In test A: an average IC$_{50}$ of $1.7 \times 10^{-8}$M;

In test B an average pA$_2$ of 8.95;

In test C: ED$_{50}$ of 0.5 mg/kg (i.v. administration).

The compounds of formula I will generally be administered for therapeutic or prophylactic purposes to warm-blooded animals (including man) requiring such treatment in the form of a pharmaceutical composition, as is well known in the pharmaceutical art. According to a further feature of the invention there is provided a pharmaceutical composition comprising a compound of formula I, or a salt thereof as defined above, together with a pharmaceutically acceptable diluent or carrier. Such compositions will conveniently be in a form suitable for oral administration (e.g. as a tablet, capsule, solution, suspension or emulsion) or parenteral administration (e.g. as an injectable aqueous or oily solution, or injectable emulsion).

The compounds of formula I may also be advantageously administered for therapeutic or prophylactic purposes together with another pharmacological agent known in the general art to be of value in treating one or more of the diseases or medical conditions referred to hereinabove.

In general a compound of formula I (or a pharmaceutically acceptable salt thereof as appropriate) will generally be administered to man so that, for example, a daily oral dose of up to 50 mg/kg body weight (and preferably of up to 10 mg/kg) or a daily parenteral dose of up to 5 mg/kg body weight (and preferably of up to 1 mg/kg) is received, given in divided doses as necessary, the precise amount of compound (or salt) administered and the route and form of administration depending on size, age and sex of the person being treated and on the particular disease or medical condition being treated according to principles well known in the medical arts.

In addition to their aforesaid use in therapeutic medicine in humans, the compounds of formula I are also useful in the veterinary treatment of similar conditions affecting commercially valuable warm-blooded animals, such as dogs, cats, horses and cattle. In general for such treatment, the compounds of the formula I will generally be administered in an analogous amount and manner to those described above for administration to humans. The compounds of formula I are also of value as pharmacological tools in the development and standardisation of test systems for the evaluation of the effects of AII in laboratory animals such as cats, dogs, rabbits, monkeys, rats and mice, as part of the continuing search for new and improved therapeutic agents.

The invention will now be illustrated by the following non-limiting Examples in which, unless otherwise stated:—

(i) concentrations and evaporations were carried out by rotary evaporation in vacuo;

(ii) operations were carried out at room temperature, that is in the range 18°–26° C.;

(iii) flash column chromatography was performed on Merck Kieselgel 60 (Art. no. 9385) obtained from E Merck, Darmstadt, Germany;

(iv) yields, where given, are intended for the assistance of the reader only and are not necessarily the maximum attainable by diligent process development;

(v) $^1$H NMR spectra were normally determined at 200 MHz in CDCl$_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet;

(vi) $^{13}$C NMR spectra were normally determined at 100 MHz in CDCl$_3$ or d$_6$-dimethylsulphoxide (d$_6$-DMSO) using the solvent signal as internal standard, and are expressed as chemical shifts (delta values) in parts per million relative to TMS;

(vii) all end-products had satisfactory microanalyses; and (viii) the term "1H-tetrazol-5-yl" stands for "1H-1,2,3,4-tetrazol-5-yl".

EXAMPLE 1

1.25M sodium hydroxide solution (2.4 ml) was added to a solution of methyl 4'-[(2-ethylquinolin-4-yloxy)methyl]biphenyl-2- carboxylate (A) (380 mg) in ethanol (5 ml). The solution was heated under reflux for 2 hours and then volatile material was removed by evaporation. The residue was dissolved in water (30 ml) and the solution acidified to pH 4 with 2M hydrochloric acid. The precipitated solid was a collected, dried under high vacuum and recrystallised from ethanol to give 4'-[(2-ethylquinolin-4-yloxy)methyl]biphenyl-2-carboxylic acid (254 mg), as white crystals, m.p. 204°–205° C.; NMR (d$_6$-dimethylsulphoxide (d$_6$-DMSO)): 1.34(t,3H), 2.9(q,2H), 5.42(s,2H), 7.1(s,1H), 7.38–7.78(complex m,10H), 7.88(d,1H), 8.15(dd,1H), 12.74(br,1H); mass spectrum (negative fast atom bombardment [-ve FAB], DMSO/glycerol (GLY): 382 (M-H)$^-$, 172; microanalysis found: C,78.0; H,5.4; N,4.05; C$_{25}$H$_{21}$NO$_3$ requires: C,78.3; H,5.5; N,3.7%.

The starting material (A) was obtained as follows:—
(i) A 1.6M solution of butyllithium in hexane (24.0 ml) was added dropwise to a stirred solution of 4-bromotoluene (6.0 g) in dry tetrahydrofuran (THF) (50 ml) at −78° C. under an atmosphere of argon. The temperature was maintained at −78° C. for 20 minutes and then a 1M solution of anhydrous zinc chloride in ether (38.6 ml) was added. The solution was kept at −78° C. for 15 minutes, and then tetrakis (triphenylphosphine)palladium (60 mg) in THF (5 ml) was added, followed by methyl-2-iodobenzoate (6.1 g) in THF (10 ml). The solution was allowed to reach ambient temperature over 1 hour, then heated under reflux for 5 hours. The solvent was removed by evaporation and the residue was dissolved in chloroform (150 ml). The solution was washed with a solution of ethylene diaminetetracetic acid (10 g) in water (100 ml) and the aqueous layer was re-extracted with chloroform (100 ml). The combined organic extracts were dried (MgSO$_4$) and the solvent removed by evaporation. The residue was purified by flash chromatography, eluting with ethyl acetate/hexane (1:9 v/v) to give methyl 4'-methylbiphenyl-2-carboxylate (B) as a colourless oil (4.4 g); NMR: 2.4(s,3H), 3.65(s,3H), 7.2(s,4H), 7.35(m,3H), 7.5(m,1H), 7.8(d,1H).

(ii) N-Bromosuccinimide (8.1 g) and azo(bisisobutyronitrile) (130 mg) were added to a solution of compound (B) (9.3 g) in carbontetrachloride (300 ml). The mixture was heated under reflux for 4 hours and then cooled to ambient temperature. Insoluble material was removed by filtration and the filtrate concentrated. The residue was purified by flash chromatography, eluting with ethyl acetate/hexane (1:9 v/v) to give methyl 4'-(bromomethyl)biphenyl-2-carboxylate (C) as a solid (10.9 g), m.p. 48°–50° C.; NMR: 3.65(s,3H), 4.55(s,2H), 7.25–7.60 complex (m,7H), 7.85(d,1H).

(iii) Sodium hydride (60% dispersion in mineral oil; 60 mg) was added to a stirred solution of 2-ethyl-4-quinolone (260 mg) prepared by the method described in *Org. Syn.*, 1955, Coll. Vol. III, p.374 and p593), in N,N-dimethylformamide (DMF)(2.5 ml). The mixture was stirred until evolution of hydrogen had ceased and then a solution of the bromomethyl compound (C) (460 mg) in DMF (1 ml) was added. The reaction mixture was stirred for 16 hours. The solvent was removed by evaporation and the residue was partitioned between water (10 ml) and ethyl acetate (2×5 ml). The organic phase was washed with water, followed by saturated sodium chloride solution and dried (MgSO$_4$). The solvent was evaporated and the residue purified by flash chromatography, eluting with ethyl acetate/dichloromethane (1:4 v/v) to give methyl 4'-[(2-ethylquinolin-4-yloxy)methyl]biphenyl-2-carboxylate (A) as a solid (385 mg), m.p. 132°–134° C.; NMR: 1.41(t,3H), 2.97(q,2H), 3.68(s,3H), 5.34(s,2H), 6.77(s,1H), 7.44–7.7(complex m,9H), 7.87(dd,1H), 8.0(d,1H), 8.26(dd,1H); mass spectrum (positive chemical ionisation [+ve CI]: 398 (M+H)$^+$, 225, 174; $^{13}$C NMR: (benzylic CH$_2$) 69.73.

EXAMPLES 2–4

Using a similar procedure to that described in Example 1, but starting from the appropriate ester of the formula II in which is a methoxycarbonyl group the following compounds were obtained:—

(Example 2): 4'-[(2-Methylquinolin-4-yloxy)methyl]-biphenyl-2-carboxylic acid hydrochloride, m.p. 184°–186° C.; NMR (d$_6$-DMSO): 2.93(s,3H), 5.67(s,2H), 7.38–7.72(m,8H), 7.77(dd,1H), 7.84(dd,1H), 8.08(dt,1H), 8.29(d,1H), 8.33(d,1H); mass spectrum (-ve FAB, DMSO/m-nitrobenzyl alcohol)(NBA): 368 (M-H)$^-$; microanalysis found: C,71.2; H,5.0; N,3.6; Cl, 8.6%, C$_{24}$H$_{19}$NO$_3$.HCl requires: C,71.0; H,5.0; N,3.5; Cl,8.7%; starting from methyl 4'-[(2-methylquinolin-4-yloxy)methyl]biphenyl-2-carboxylate, obtained as a solid, m p 146° C.; NMR: 2.71(s,3H), 3.67(s,3H), 5.33(s,2H), 6.74(s,1H), 7.3–7.6(complex m,8H), 7.68(dt,1H), 7.87(dd,1H), 7.98(d,1H), 8.23(dd,1H); itself obtained from 2-methyl-4-quinolone, using analogous procedures to those described in Example 1;

(Example 3): 4'-[(2-Propylquinolin-4-yloxy)methyl]-biphenyl-2-carboxylic acid*, m.p. 198°–200° C.; NMR (d$_6$-DMSO): 0.97(t,3H), 1.8(m,2H), 2.85(t,2H), 5.43(s,2H), 7.08(s,1H), 7.35–7.65(complex m,8H), 7.73(dt,2H),7.87(d,1H), 8.15(dd,1H), 12.7(br s,1H); mass spectrum (-ve FAB, DMSO/GLY): 396 (M-H)$^-$, 186; microanalysis, found: C,77.5; H,6.0; N,3.5%; C$_{26}$H$_{23}$NO$_3$.0.33C$_2$H$_5$OH requires: C,77.8; H,6.1; N,3,4%; starting from methyl 4'-[(2-propylquinolin-4-yloxy)methyl]biphenyl-2-carboxylate, obtained as a viscous oil; NMR: 1.03(t,3H), 1.87(m,2H), 2.94(t,2H), 3.68(s,3H), 5.36(s,2H), 6.75(s,1H), 7.34–7.6(complex m,8H), 7.68(dt,1H), 7.85(dd,21H), 8.03(d,1H), 8.25(dd,1H); $^{13}$C NMR (CDCl$_3$): (benzylic CH$_2$) 69.8; itself obtained from 2-propyl-4-quinolone using analogous procedures to those described in Example 1; [*Note: 1M aqueous citric acid solution was used in place of 2M hydrochloric acid in the work-up procedure].

(Example 4): 4'-[(2-Butylquinolin-4-yloxy)methyl]-biphenyl-2-carboxylic acid, m.p. 148° C.; NMR (d$_6$-DMSO): 0.93(t,3H), 1,38(m,2H), 1.8(m,2H), 2.95(t,2H), 5.5(s,2H), 7.25(s,1H), 7.33–7.68(complex m,8H), 7.7–7.85(m,2H), 7.98(d,1H), 8.2(d,1H); mass spectrum (-ve FAB, DMSO/GLY): 410 (M-H)$^-$, 200; microanalysis found: C,77.1; H,6.1; N,3.1%; C$_{27}$H$_{25}$NO$_3$.0.5H$_2$O requires: C,77.1; H,6.2; N,3.3%; starting from methyl 4'-[(2-butylquinolin-4-yloxy)methyl]biphenyl-2-carboxylate obtained as viscous oil; NMR: 0.97(t,3H), 1.45(m,2H), 1.78(m,2H), 2.94(t,2H), 3.68(s,3H), 5.35(s,2H), 6.76(s,1H), 7.35–7.6(complex m,8H), 7.69(dt,1H), 7.88(dd,1H), 8.0(d,1H), 8.25(dd,1H); mass spectrum (+ve CI): 426 (M+H)$^+$, 225, 202; itself obtained from 2-butyl-4-quinolone using analogous procedures to those described in Example 1.

The starting materials, 2-methyl-4-quinolone and 2-propyl-4-quinolone, were obtained as described in *Org. Syn.*, 1955 Coll. Vol. III, page 374 and page 593. 2-Butyl-4-quinolone was obtained using an analogous procedure, starting from ethyl 3-oxoheptanoate and had the following NMR spectrum: 0.88(t,3H), 1.34(m,2H), 1.7(m,2H), 2.7(t,2H), 6.27(s,1H), 7.34(t,1H), 7.6(dt,1H)), 7.78(d,1H), 8.36(d,1H), 11.8(br s, 1H).

EXAMPLE 5

5M Aqueous sodium hydroxide solution (2 ml) was added to a solution of methyl 4-[(2-propylquinolin-4- yloxy)methyl]benzoate (A) (500 mg) in methanol (5 ml). the solution was allowed to stand for 16 hours. Water (50 ml) was added and the mixture heated to dissolve the solid precipitate. The solution was filtered and the filtrate acidified to pH4 with 1M aqueous citric acid solution. The precipitated solid was collected by filtration and dried under high vacuum to give 4-[(2-propylquinolin-4-yloxy)methyl]benzoic acid (347 mg), as a white powder, m.p. 225°–227° C.; NMR (d$_6$-DMSO): 0.95(t,3H), 1.7–1.9(m,2H), 2.84(t,2H), 5.5(s,2H), 7.05(s,1H), 7.5(dt,1H), 7.7(m,3H), 7.88(d,1H), 8.0(d,1H), 8.15(dd,1H), 12.9(br,1H); mass spectrum (-ve FAB, DMSO/Gly); 32) (M-H)$^-$, 186; microanalysis found: C,73.9; H,5.9; N,4.2%; C$_{20}$H$_{19}$NO$_3$.0.25H$_2$O requires; C,73.7; H,6.0; N,4.3%.

The starting ester (A) was obtained from 2-propyl-4-quinolone (561 mg) and methyl 4-(bromomethyl)benzoate (700 mg) together with appropriate amount to the other necessary agents and solvents, using a similar procedure to that described in Example 1, part (iii) and purification by flash chromatography eluting with a mixture of methanol and dichloromethane (1:9 v/v), as a solid (540 mg), m.p. 62°–65° C.; NMR: 1.0(t,3H), 1.83(m,2H), 2.9(t,2H), 3.95(s,3H), 5.37(s,2H), 6.69(s,1H), 7.46(dt,1H), 7.58(d,2H), 7.67(dt,1H), 8.0(d,1H), 8.1(d,2H), 8.2(dd,1H).

EXAMPLE 6

4-[(2-Propylquinolin-4-yloxy)methyl]benzoic acid (240 mg) was added to a mixture of benzene sulphonamide (120 mg), 4-dimethylaminopyridine (90 mg) and 1-[3-(dimethylamino)propyl]-3-ethylcarbodiimide hydrochloride (150 mg) in dichloromethane (20 ml) and the mixture stirred overnight. Chloroform (20 ml) was added the mixture was washed successively with 1M citric acid solution (10 ml), water (2×10 ml), saturated sodium chloride solution (5 ml) and then dried (MgSO$_4$). The solvent was removed by evaporation and the residue triturated with methanol to give 4-[(2-propylquinolin-4-yloxy)methyl]-N-phenylsulphonyl-benzamide as a white powder (160 mg), m.p. 140° C. (dec.); NMR (d$_6$-DMSO): 0.95(t,3H), 1.79(m,2H), 2.88(t,2H), 5.5(s,2H), 7.14(s,1H), 7.5–7.7(m,6H), 7.78(dt,1H), 7.87–8.02(m,5H), 8.18(dd,1H); mass spectrum (-ve FAB, DMSO/Gly): 495 (M-H)$^-$; microanalysis found: C,66.1; H,5.4; N,5.8%; C$_{26}$H$_{24}$N$_2$O$_4$S.0.5-H$_2$O requires: C,66.5; H,5.3; N,6.0%.

EXAMPLE 7

A mixture of 2-methyl-4-[(2'-(2-triphenylmethyl-2H-tetrazol-5-yl)biphenyl-4-yl)methoxy]quinoline (A) (890 mg) and a 7.5M solution of hydrogen chloride dioxane (10 ml) and water (1 ml) was allowed to stand for 72 hours. Volatile material was removed by evaporation and the residue was triturated with ether (2×50 ml). The ether was decanted off and the solid residue crystallised from isopropanol to give 2-methyl-4-[(2'-(1H-tetrazol-5-yl)biphenyl-4-yl)methoxy]quinoline hydrochloride (370 mg), as a white solid, m.p. 188°–190° C.; NMR (d$_6$-DMSO): 2.92(s,3H), 5.63(s,2H), 7.21(d,2H), 7.56–7.87(m,8H), 8.07(dt,1H), 8.28(dd,1H), 8.32(dd,1H); mass spectrum [-ve FAB, DMSO/NBA]: 392 (M-H)$^-$, 158; microanalysis found: C,66.0; H,4.6; N,15.5%; C$_{24}$H$_{19}$N$_5$O.HCl.0.5H$_2$O requires: C,65.7; H,4.8; N,16.0%.

The starting material (A) was obtained as follows:—

Sodium hydride (60% dispersion in mineral oil; 90 mg) was added to a stirred solution of 2-methyl-4-quinolone (340 mg) in DMF (10 ml). The mixture was stirred until evolution of hydrogen had ceased and a solution of 5-2-(4'-bromomethylbiphenylyl)]-2-triphenylmethyl-2H tetrazole (1.2 g) (obtained as described in European Patent 0291969) in DMF (5 ml) was added. The mixture was stirred for 16 hours. The solvent was removed by evaporation and the residue partitioned between water (20 ml) and dichloromethane (2×10 ml). The organic layer was washed with saturated sodium chloride solution (5 ml) and dried (MgSO$_4$). The solvent was removed by evaporation and the resultant oil was purified by flash chromatography, eluting with methanol/dichloromethane (1:99 v/v) to give 2-methyl-4-[2'-(2-triphenylmethyl-2H-tetrazol-5-yl)biphenyl-4-ylmethoxy]-quinoline (A) (890 mg) as a white solid m.p. 168°–170° C. (dec.); NMR: 2.7(s,3H), 5.14(s,2H), 6.7(s,1H), 6.9(dd,6H), 7.15–7.55(complex m,17H), 7.65(dt,1H), 7.95(m,2H), 8.1(dd,1H).

EXAMPLE 8

Using an analogous procedure to that described in Example 7 but starting from 2-propyl-4-[(2'-(2-triphenylmethyl-2H-tetrazol-5-yl)biphenyl-4-yl)methoxy]quinoline (A), there was obtained 2-propyl-4-[(2'-(1H-tetrazol-5-yl)biphenyl-4-yl)methoxy]quinoline hydrochloride, m.p 178°–180° C.; NMR (d$_6$-DMSO): 0.98(t,3H), 1.88(m,2H) 3.08(t,2H), 5.6(s,2H), 7.2(d,2H), 7.5–7.85(complex m,8H), 8.02(dt,1H), 8.2(d,1H), 8.28(dd,1H); mass spectrum (-ve FAB, DMSO/NBA): 420(M-H)$^-$; microanalysis found: C,67.9; H,5.2; N,14.9%; C$_{26}$H$_{23}$N$_5$O.HCl requires C,68.2; H,5.3; N,15.3%.

The starting material (A) was obtained as white solid, m.p. 150°–152° C.; NMR: 1.05(t,3H), 1.88(m,2H), 2.92(t,2H), 5.2(s,2H), 6.73(s,1H), 6.94(dd,6H), 7.15–7.58(complex m,17H), 7.68(dt,1H), 8.0(m,2H), 8.12(dd,1H), $^{13}$C NMR (CDCl$_3$): (benzylic CH$_2$) 69.67; starting from 2-propyl-4-quinolone using a similar procedure to that described in Example 7.

EXAMPLES 9–29

Using an analogous procedure to that described in Example 7, but starting from the appropriate triphenylmethyl tetrazoles (III), the following compounds of formula I were obtained in yields of 70–90%:—

(Example 9): 5-Cyano-2-ethyl-4- [(2'-(1H-tetrazol-5-yl)biphenyl-4-yl)methoxy]quinoline hydrochloride, m.p. 240° C. (dec); NMR (d$_6$-DMSO): 1.40(t,3H), 3.16(q,2H), 5.57(s,2H), 7.17(d,2H), 7.50–7.75(m,7H), 8.10(t,1H), 8.32(d,1H), 8.62(d,1H); mass spectrum (-ve FAB, DMSO/GLY): 431 (M-H)$^-$; microanalysis, found: C,65.2; H,4.5; N,16.6; H$_2$O,2.0%; C$_{26}$H$_{20}$N$_6$O.HCl.0.5H$_2$O requires: C,64.9; H,4.8; N,16.8; H$_2$O,1.8%;

(Example 10): 2-Ethyl-6-trifluoromethyl-4-[(2'-(1H-tetrazol-5-yl)biphenyl-4-yl)methoxy]quinoline hydrochloride, m.p. 188°–190° C.; NMR (d$_6$-DMSO): 1.43(t,3H), 3.20(q,2H), 5.67(s,2H), 7.20(d,2H), 7.55–7.73(m,7H), 8.30(d,1H), 8.48(d,2H); mass spectrum (-ve FAB, DMSO/GLY): 474 (M-H)$^-$; microanalysis, found: C,60.6; H,3.9; N,13.3%; C$_{26}$H$_{20}$N$_5$OF$_3$.HCl requires: C,61.0; H,4.1; N,13.7%;

(Example 11): 2-Ethyl-8-trifluoromethyl-4-[(2'-(1H-tetrazol-5-yl)biphenyl-4-yl)methoxy]quinoline*, m.p. 110°–113° C.; NMR (CDCl$_3$): 1.42(t,3H), 3.05(q,2H), 5.37(s,2H), 6.85(s,1H), 7.28–7.62(m,8H), 8.03(d,1H), 8.14(dd,1H), 8.43(d,1H); mass spectrum (-ve FAB, DMSO/GLY): 474 (M-H)$^-$; microanalysis, found:

C,64.6; H,4.4; N,13.3%; $C_{26}H_{20}N_5OF_3$. 0.67 dioxane requires C,64.5; H,4.7; N,13.1%. *Isolated as free base;

(Example 12): 2-Ethyl-6-methoxy-4-[(2'-(1H-tetrazol-5-yl)biphenyl-4-yl)methoxy]quinoline hydrochloride, m.p. 213°–215° C.; NMR (d$_6$-DMSO): 1.41(t,3H), 3.12(q,2H), 3.95(s,3H), 5.68(s,2H), 7.20(d,2H), 7.50-7.76(m,9H), 8.21(d,1H); mass spectrum (-ve FAB, DMSO/GLY): 436 (M-H)$^-$; microanalysis, found: C,66.1; H,5.0; N,14.6%; $C_{26}H_{23}N_5O_2$.HCl. requires C,65.9; H,5.1; N,14.8%;

(Example 13): 2-Ethyl-8-methoxy-4-[(2'-(1H-tetrazol-5-yl)biphenyl-4-yl)methoxy]quinoline hydrochloride, m.p. 125°–127° C.; NMR (d$_6$-DMSO): 1.40(t,3H), 3.24(q,2H), 4.14(s,3H), 5.66(s,2H), 7.21(d,2H), 7.50-7.84(m,10H); mass spectrum (-ve FAB, DMSO/GLY): 436 (M-H)$^-$; microanalysis, found: C,63.7; H,5.8; N,13.5%; $C_{26}H_{23}N_5O_2$.HCl.0.5H$_2$O.0.5dioxane requires C,63.8; H,5.3; N,13.3%.

(Example 14): 2-Ethyl-5,7-dimethoxy-4-[(2'-(1H-tetrazol-5-yl)biphenyl-4-yl)methoxy]quinoline hydrochloride, m.p. 203°–205° C.; NMR (d$_6$-DMSO): 1.40(t,3H), 3.07(q,2H), 3.91(s,3H), 3.94(s,3H), 5.56(s,2H), 6.80(d,1H), 7.21(d,2H), 7.31(s,2H), 7.51(d,2H), 7.56-7.62(m,2H), 7.68-7.75(m,2H); mass spectrum (-ve FAB, DMSO/GLY): 466(M-H)$^-$; microanalysis, found: C,63.6; H,5.3; N,12.9; H$_2$O,1.0%; $C_{27}H_{25}N_5O_3$.HCl.0.25H$_2$O.0.25dioxane requires C,63.5; H,5.2; N,13.2; H$_2$O,0.9%;

(Example 15): 2-Ethyl-6,7-dimethoxy-4-[(2'-(1H-tetrazol-5-yl)biphenyl- 4-yl)methoxy]quinoline hydrochloride, m.p. 272° C. (decomp); NMR (d$_6$DMSO): 1.40(t,3H), 3.10(q,2H), 3.95(s,3H), 3.98(s,3H), 5.65(s,2H), 7.20(d,2H), 7.43(d,2H), 7.53-7.74(m,7H); mass spectrum (-ve FAB, DMSO/GLY): 466(M-H)$^-$; microanalysis, found: C,62.7; H,5.1; N,13.5; H$_2$O,2.5%; $C_{27}H_{25}N_5O_3$.HCl.0.75H$_2$O requires C,62.7; H,5.1; N,13.5; H$_2$O,2.6%;

(Example 16): 2-Ethyl-5,8-dimethoxy-4-[(2'-(1H-tetrazol-5-yl)biphenyl-4-yl)methoxy]quinoline hydrochloride, m.p. 171° C. (decomp.); NMR (d$_6$-DMSO): 1.39(t,3H), 3.22(q,2H), 3.90(s,3H), 4.09(s,3H), 5.62(s,2H), 7.19-7.28(m,3H), 7.51-7.77(m,8H); mass spectrum (-ve FAB, DMSO/GLY): 466 (M-H)$^-$; microanalysis, found: C,61.3; H,5.4; N,12.9; H$_2$O,5.8%; $C_{27}H_{25}N_5O_3$.HCl.1.5H$_2$O requires C,61.1; H,5.3; N,13.2; H$_2$O, 5.1%;

(Example 17): 2-Ethyl-5,6,7-trimethoxy-4-[(2'-(1H-tetrazol-5-yl)biphenyl-4-yl)methoxy]quinoline hydrochloride, m.p. 181°–182° C.; NMR (d$_6$-DMSO): 1.42(t,3H), 3.10(q,2H), 3.68(s,3H), 3.87(s,3H), 4.00(s,3H), 5.55(s,2H), 7.20(d,2H), 7.42(s,1H), 7.53-7.62(m,5H), 7.68-7.74(m,2H); mass spectrum (-ve FAB, DMSO/GLY): 496 (M-H)$^-$; microanalysis, found: C,60.6; H,5.1; N,12.6; H$_2$O,2.9%; $C_{28}H_{27}N_5O_4$.HCl.H$_2$O requires C,60.9; H,5.3; N,12.7; H$_2$O,3.3%;

(Example 18): 7-Cyano-2-ethyl-4-[(2'-(1H-tetrazol-5-yl)biphenyl-4-yl)methoxy]quinoline hydrochloride, m.p. 160°–163° C.; NMR (d$_6$-DMSO): 1.43(t,3H), 3.17(q,2H), 5.64(s,2H), 7.20(d,2H), 7.55(d,2H), 7.58-7.72(m,5H), 8.08(d,1H), 8.40(d,1H), 8.76(s,1H); mass spectrum (-ve FAB, DMSO/GLY): 431 (M-H)$^-$; microanalysis, found: C,64.3; H,4.9; N,16.6%; $C_{26}H_{20}N_6O$.HCl.H$_2$O.0.1dioxane requires C,64.1; H,4.8; N,17.0%;

(Example 19): 2-Ethyl-7-methoxy-4-[(2'-(1H-tetrazol-5-yl)biphenyl-4-yl)methoxy]quinoline hydrochloride, m.p. 172°–174° C.; NMR(d$_6$-DMSO): 1.44(t,3H), 3.15(q,2H), 3.97(s,3H), 5.64(s,2H), 7.21(d,2H), 7.38-7.77(m,9H), 8.20(d,1H); mass spectrum (-ve FAB, DMSO/GLY): 436(M-H)$^-$; microanalysis, found: C,63.8; H,5.5; N,13.8; H$_2$O,3.5%; $C_{26}H_{23}N_5O_2$.HCl.H$_2$O requires C,63.5; H,5.3; N,14.2; H$_2$O,3.7%;

(Example 20): 6-Carbomethoxy-2-ethyl-4-[(2'-(1H-tetrazol-5-yl)biphenyl-4-yl)methoxy]quinoline hydrochloride, m.p. 202°–204° C.; NMR (d$_6$-DMSO): 1.50(t,3H), 3.28(q,2H), 4.00(s,3H), 5.74(s,2H), 7.29(d,2H), 7.56-7.82(m,7H), 8.48-8.55(m,2H), 8.82(s,1H); mass spectrum (-ve FAB, DMSO/GLY): 464 (M-H)$^-$; microanalysis, found: C,64.6; H,4.7; N,13.8%; $C_{27}H_{23}N_5O_3$.HCl requires C,64.6; H,4.8; N,14.0%;

(Example 21): 2-Ethyl-5-methyl-4-[(2'-(1H-tetrazol-5-yl)biphenyl-4-yl)- methoxy]quinoline hydrochloride, m.p. 168°–169° C. (dec.); NMR (d$_6$-DMSO): 1.42(t,3H), 2.75(s,3H), 3.17(q,2H), 5.61(s,2H), 7.20(d,2H), 7.54-7.71(m,8H), 7.89(t,1H), 8.19(d,1H); mass spectrum (-ve FAB, DMSO/GLY): 420 (M-H)$^-$; microanalysis, found: C,65.8; H,5.4; N,14.0; H$_2$O,3.0%; $C_{26}H_{23}N_5O$.HCl.0.75H$_2$O.0.33 EtOAc requires C,65.6; H,5.6; N,14.0; H$_2$O,2.7%;

(Example 22): 2-Ethyl-7-methyl-4-[(2'-(1H-tetrazol-5-yl)biphenyl-4-yl)methoxy]quinoline hydrochloride, m.p. 213°–215° C. (dec.); NMR (d$_6$-DMSO): 1.43(t,3H), 2.59(s,3H), 3.19(q,2H), 5.65(s,2H), 7.22(d,2H), 7.54-7.75(m,8H), 8.09(s,1H), 8.19(d,1H); mass spectrum (-ve FAB, DMSO/GLY): 420 (M-H)$^-$; microanalysis, found: C,68.5; H,5.3; N,15.3%; $C_{26}H_{23}N_5O$.HCl requires C,68.2; H,5.3; N,15.3%;

(Example 23): 2,6-Dimethyl-4-[(2'-(1H-tetrazol-5-yl)biphenyl-4-yl)methoxy]quinoline hydrochloride, m.p. 200°–202° C. (dec.); NMR (d$_6$-DMSO): 2.56(s,3H), 2.89(s,3H), 5.62(s,2H), 7.22(d,2H), 7.54-7.72(m,7H), 7.91(dd,1H), 8.06(s,1H), 8.18(d,1H); mass spectrum (-ve FAB, DMSO/GLY): 406 (M-H)$^-$; microanalysis, found: C,67.1; H,4.8; N,15.4%; $C_{25}H_{21}N_5O$.HCl.0.25-H$_2$O requires C,67.0; H,5.0; N,15.6%;

(Example 24): 2,8-Dimethyl-4-[(2'-(1H-tetrazol-5-yl)biphenyl-4-yl)methoxy]quinoline hydrochloride, m.p. 193°–195° C. (dec.); NMR (d$_6$-DMSO): 2.82(s,3H), 2.99(s,3H), 5.63(s,2H), 7.21(d,2H), 7.53-7.72(m,8H), 7.89(d,1H), 8.16(d,1H); mass spectrum (-ve FAB, DMSO/GLY): 406 (M-H)$^-$; microanalysis, found: C,67.5; H,5.0; N,15.6%; $C_{25}H_{21}N_5O$.HCl requires C,67.6; H,5.0; N,15.8%;

(Example 25): 2-Ethyl-4-[(2'-(1H-tetrazol-5-yl)biphenyl-4-yl)methoxy]quinoline hydrochloride, m.p. 178°–181° C. (dec.); NMR (d$_6$-DMSO): 1.48(t,3H), 3.22(q,2H), 5.68(s,2H), 7.23(d,2H), 7.5-7.8(m,7H), 7.83(t,1H), 8.08(t,1H), 8.32(t,2H); $^{13}$C NMR: (benzylic CH$_2$) 71.9; mass spectrum (-ve FAB, DMSO/GLY): 406 (M-H)$^-$; microanalysis, found: C,68.0; H,5.1; N,15.8%; $C_{25}H_{21}N_5O$.HCl requires C,67.6; H,5.0; N,15.8%.

(Example 26): 6,8-Dimethyl-2-ethyl-4-[(2'-(1H-tetrazol-5-yl)biphenyl-4-yl)methoxy]quinoline hydrochloride, m.p. 195°–197° C. (dec.); NMR (d$_6$-DMSO): 1.4(t,3H), 2.5(s,3H), 2.81(s,3H), 3.34(q,2H), 5.65(s,2H), 7.22(d,2H), 7.54-7.72(m,8H), 7.89(s,1H); mass spectrum (-ve FAB, DMSO/GLY): 434 (M-H)$^-$; microanalysis, found: C,68.7; H,5.6; N,14.8%; $C_{27}H_{25}N_5O$.HCl requires C,68.7; H,5.5; N,14.9%;

(Example 27): 6-Chloro-2-methyl-4-[(2'-(1H-tetrazol-5-yl)biphenyl-4-yl)methoxy]quinoline hydrochloride m.p. 197°–198° C. (dec.); NMR (d$_6$-DMSO): 2.9(s,3H), 5.61(s,2H), 7.22(d,2H), 7.53-7.77(m,7H), 8.08(dd,1H), 8.21-8.28(m,2H); $^{13}$C NMR: (benzylic CH$_2$) 72; mass spectrum (-ve FAB, DMSO/GLY): 426 (M-H)$^-$; microanalysis, found: C,62.2; H,4.1; N,15.1; Cl,15.0%; $C_{24}H_{18}N_5ClO\cdot HCl$ requires C,62.1; H,4.1; N,15.1; Cl,15.3%;

(Example 28): 7-Chloro-2-ethyl-4-[(2'-(1H-tetrazol-5-yl)biphenyl-4-yl)methoxy]quinoline hydrochloride m.p. 170°–172° C. (dec.); NMR ($d_6$-DMSO): 1.43(t,3H), 3.18(q,2H), 5.64(s,2H), 7.21(d,2H), 7.5–7.75(m,7H), 7.81(dd,1H), 8.29(d,1H), 8.40(d,1H); mass spectrum (-ve FAB, DMSO/GLY): 440 (M-H)$^-$; microanalysis, found: C,61.8; H,4.3; N,14.2; Cl,14.3; $H_2O$,2.1%; $C_{25}H_{20}N_5ClO\cdot HCl\cdot 0.5H_2O$ requires C,61.6; H,4.5; N,14.4; Cl,14.6; $H_2O$,1.8%; and (Example 29): 8-Chloro-2-ethyl-4-[(2'-(1H-tetrazol-5-yl)biphenyl-4-yl)methoxy]quinoline hydrochloride m.p. 146°–148° C. (dec.); NMR ($d_6$-DMSO): 1.38(t,3H), 3.08(q,2H), 5.52(s,2H), 7.19(d,2H), 7.38(t,1H), 7.51–7.75(m,7H), 8.02(d,1H), 8.18(dd,1H); mass spectrum (-ve FAB, DMSO/GLY): 440(M-H)$^-$; microanalysis, found: C,60.8; H,4.6; N,14.1%; $C_{25}H_{20}N_5ClO\cdot HCl\cdot H_2O$ requires C,60.5; H,4.6; N,14.1%.

The necessary starting materials of formula III were obtained in yields of 20–70% using an analogous procedure to that described in Example 7 but starting from the appropriate quinolines of formula IV. The compounds of formula III had the following properties:

(9): 5-Cyano-2-ethyl-4-([2'-(2-triphenylmethyl-2H-tetrazol-5-yl)biphenyl-4-yl]methoxy)quinoline, isolated as a foam; NMR ($d_6$-DMSO): 1.34(t,3H), 2.96(q,2H), 5.55(s,2H), 6.82–6.93(m,6H), 7.14(d,2H), 7.25–7.36(m,9H), 7.40–7.65(m,6H), 7.80(dd,1H), 7.93(t,1H), 8.16(d,1H), 8.30(d,1H);

(10): 2-Ethyl-6-trifluoromethyl-4-([2'-(2-triphenylmethyl-2H-tetrazol-5-yl)biphenyl-4-yl]methoxy)quinoline, isolated as a foam; NMR: 1.55(t,3H), 3.12(q,2H), 5.35(s,2H), 6.91(s,1H), 7.05–7.10(m,6H), 7.33–7.45(m,13H), 7.52–7.69(m,3H), 7.99(dd,1H), 8.10(dd,1H), 8.24(d,1H), 8.64(s,1H);

(11): 2-Ethyl-8-trifluoromethyl-4-([2'-(2-triphenylmethyl-2H-tetrazol-5-yl)biphenyl-4-yl]methoxy)quinoline, isolated as a foam; NMR: 1.45(t,3H), 3.01(q,2H), 5.19(s,2H), 6.80(s,1H), 6.88–7.0(m,6H), 7.18–7.55(m,17H), 8.05(dd,2H), 8.32(d,1H); $^{13}$C NMR: (benzylic $CH_2$) 69.96;

(12): 2-Ethyl-6-methoxy-4-([2'-(2-triphenylmethyl-2H-tetrazol-5-yl)biphenyl-4-yl]methoxy)quinoline, isolated as a foam; NMR: 1.37(t,3H), 2.90(q,2H), 3.80(s,3H), 5.19(s,2H), 6.70(s,1H), 6.91–6.97(m,6H), 7.19–7.35(m,14H), 7.42–7.52(m,4H), 7.89–7.95(m,2H); $^{13}$C NMR: (benzylic $CH_2$) 69.72;

(13): 2-Ethyl-8-methoxy-4-([2'-(2-triphenylmethyl-2H-tetrazol-5-yl)biphenyl-4-yl]methoxy)quinoline, isolated as a foam; NMR ($d_6$-DMSO): 1.33(t,3H), 2.88(q,2H); 3.93(s,3H), 5.31(s,2H), 6.81–6.92(m,6H), 7.10–7.12(m,4H), 7.25–7.70(m,15H), 7.85(d,2H);

(14): 2-Ethyl-5,7-dimethoxy-4-([2'-(2-triphenylmethyl-2H-tetrazol-5-yl)biphenyl-4-yl]methoxy)quinoline, isolated as a foam; NMR: 1.39(t,3H), 2.89(q,2H), 3.87(s,3H), 3.93(s,3H), 5.14(s,2H), 6.46(d,1H), 6.58(s,1H), 6.86–6.95(m,6H), 7.01(d,1H), 7.16–7.29(m,11H), 7.35–7.52(m,5H), 7.91–7.95(m,1H); $^{13}$C NMR: (benzylic $CH_2$) 69.63;

(15): 2-Ethyl-6,7-dimethoxy-4-([2'-(2-triphenylmethyl-2H-tetrazol-5-yl)biphenyl-4-yl]methoxy)quinoline, m.p. 211° C. (decomp.); NMR ($d_6$-DMSO): 1.39(t,3H), 2.90(q,2H), 3.87(s,3H), 4.03(s,3H), 5.20(s,2H), 6.65(s,1H), 6.94–7.00(m,6H), 7.19–7.33(m,13H), 7.39–7.55(m,5H), 7.94(dd,1H); $^{13}$C NMR: (benzylic $CH_2$) 69.72;

(16): 2-Ethyl-5,8-dimethoxy-4-([2'-(2-triphenylmethyl-2H-tetrazol-5-yl)biphenyl-4-yl]methoxy)quinoline, m.p. 94°–97° C.; NMR ($CDCl_3$): 1.41(t,3H), 3.04(q,2H), 3.85(s,3H), 4.04(s,3H), 5.18(s,2H), 6.75(d,2H), 6.88–6.98(m,7H), 7.18–7.29(m,11H), 7.37–7.56(m,5H), 7.91–7.96(m,1H); $^{13}$C NMR: (benzylic $CH_2$) 69.85;

(17): 2-Ethyl-5,6,7-trimethoxy-4-([2'-(2-triphenylmethyl-2H-tetrazol-5-yl)biphenyl-4-yl]methoxy)quinoline, m.p. 90°–95° C.; NMR: 1.39(t,3H), 2.90(q,2H), 3.78(s,3H), 3.96(s,3H), 4.00(s,3H), 5.19(s,2H), 6.63(s,1H), 6.92–6.98(m, 6H), 7.18–7.56(m,17H), 7.91–7.95(m,1H); $^{13}$C NMR: (benzylic $CH_2$) 70.26;

(18): 7-Cyano-2-ethyl-4-([2'-(2-triphenylmethyl-2H-tetrazol-5-yl)biphenyl-4-yl]methoxy)quinoline*, m.p. 172°–175° C.; NMR ($d_6$-DMSO): 1.33(t,3H), 2.94(q,2H), 5.36(s,2H), 6.81–6.90(m,6H), 7.18(d,2H), 7.25–7.36(m,10H), 7.43(d,2H), 7.47–7.70(m,4H), 7.85(dd,1H), 8.13(d,1H), 8.39(d,1H);

[*Note: Prepared by alkylation of a 70:30 mixture of 7-cyano-2-ethyl-4-quinolone and 5-cyano-2-ethyl-4-quinolone and purified by flash chromatography using ethyl acetate/dichloromethane (2:98 v/v) as eluant.]

(19): 2-Ethyl-7-methoxy-4-([2'-(2-triphenylmethyl-2H-tetrazol-5-yl)biphenyl-4-yl]methoxy)quinoline*, m.p. 159°–161° C.; NMR: 1.39(t,3H), 2.92(q,2H), 3.93(s,3H), 5.12(s,2H), 6.62(s,1H), 6.90–6.95(m,7H), 7.21–7.55(m,17H), 7.95–7.80(m,2H); $^{13}$C NMR: (benzylic $CH_2$) 69.69;

[*Note: Prepared by alkylation of a 80:20 mixture of 2-ethyl-7-methoxy-4-quinolone and 2-ethyl-5-methoxy-4-quinolone and purified by flash chromatography using ethyl acetate/hexane (50:50 v/v) as eluant.]

(20): 6-Carbomethoxy-2-ethyl-4-([2'-(2-triphenylmethyl-2H-tetrazol-5-yl)biphenyl-4-yl]methoxy)quinoline, m.p. 179°–181° C.; NMR ($d_6$-DMSO): 1.33(t,3H), 2.89(q,2H), 3.85(s,3H), 5.39(s,2H), 6.81–6.95(m,6H), 7.12–7.23(m,3H), 7.24–7.38(m,9H), 7.43(d,2H), 7.50–7.69(m,3H), 7.82(dd,1H), 7.95(d,1H), 8.17(dd,1H), 8.76(d,1H);

(21): 2-Ethyl-5-methyl-4-[(2'-(2-triphenylmethyl-2H-tetrazol-5-yl)biphenyl-4-yl]methoxy)quinoline; m.p. 179°–181° C. (dec.); NMR: 1.38(t,3H), 2.78(s,3H), 2.90(m,2H), 5.15(s,2H), 6.69(s,1H), 6.9–6.98(m,6H), 7.13–7.34(m,13H), 7.4–7.57(m,5H), 7.85(d,1H), 7.94(dd,1H); $^{13}$C NMR: (benzylic $CH_2$) 70.27; microanalysis, found: C,79.3; H,5.9; N,10.5%; $C_{45}H_{37}N_5O\cdot H_2O$ requires C,79.3; H,5.7; N,10.3%;

(22): 2-Ethyl-7-methyl-4-([2'-(2-triphenylmethyl-2H-tetrazol-5-yl)biphenyl-4-yl]methoxy)quinoline; m.p. 205°–206° C. (dec.); NMR: 1.39(t,3H), 2.52(s,3H), 2.94(q,2H), 5.14(s,2H), 6.66(s,1H), 6.90–6.95(m,6H), 7.17–7.32(m,14H), 7.39–7.43(m,3H), 7.79(s,1H), 7.96–8.02(m,2H); $^{13}$C NMR: (benzylic $CH_2$) 69.69; microanalysis, found C,81.6; H,5.9; N,10.6%; $C_{45}H_{37}N_5O$ requires C,81.4; H,5.6; N,10.6%;

(23): 2,6-Dimethyl-4-([2'-(2-triphenylmethyl-2H-tetrazol-5-yl)biphenyl-4-yl]methoxy)quinoline, isolated as a foam; NMR: 2.41(s,3H), 2.69(s,3H), 5.15(s,2HO, 6.67(s,1H), 6.91–6.95(m,6HO, 7.22–7.25(m,13H), 7.44–7.51(m,4H), 7.89–7.99(m,3H);

(24): 2,8-Dimethyl-4-([2'-(2-triphenylmethyl-2H-tetrazol-5-yl)biphenyl-4-yl]methoxy)quinoline; m.p. 175°–177° C. (dec.); NMR: 2.7(s,3H), 2.78(s,3H), 5.14(s,2H), 6.69(s,1H), 6.87–6.95(m,6H), 7.15–7.3(m,14H), 7.38–7.54(m,4H), 7.94–8.02(m,2H);

microanalysis, found: C,81.6; H,5.2; N,10.9%; C₄₄H₃₅N₅O requires C,81.3; H,5.4; N,10.8%;

(25): 2-Ethyl-4-([2'-(2-triphenylmethyl-2H-tetrazol-5-yl)biphenyl-4-yl]methoxy)quinoline; m.p. 173°–174° C. (dec.); NMR: 1.4(t,3H), 2.96(q,2H), 5.16(s,2H), 6.73(s,1H), 6.9–6.94(m,6H), 7.18–7.32(m,13H), 7.33–7.55(m,4H), 7.67(dt,1H), 7.99(m,2H), 8.11(d,1H); microanalysis, found: C,81.1; H,5.4; N,10.9%; C₄₄H₃₅N₅O requires C,81.4; H,5.4; N,10.8%;

(26): 6,8-Dimethyl-2-ethyl-4-([2'-(2-triphenylmethyl-2H-tetrazol-5-yl)biphenyl-4-yl]methoxy)quinoline; m.p. 183°–185° C. (dec.); NMR: 1.4(t,3H), 2.37(s,3H), 2.76(s,3H), 2.95(q,2H), 5.13(s,2H), 6.68(s,1H), 6.90–6.95(m,6H), 7.17–7.35(m,13H), 7.43–7.50(m,4H), 7.76(s,1H), 7.95(m,1H);

(27): 6-Chloro-2-methyl-4-([2'(2-triphenylmethyl-2H-tetrazol-5-yl]methoxy)quinoline; m.p. 182°–184° C. (dec.); NMR: 2.68(s,3H), 5.15(s,2H), 6,75(s,1H), 6.87–6.97(m,6H), 7.15–7.35(m,13H), 7.4–7.62(m,4H), 7.9(d,1H), 7.98(m,1H), 8.08(d,1H);

(28): 7-Chloro-2-ethyl-4-([2'-(2-triphenylmethyl-2H-tetrazol-5-yl)biphenyl-4-yl]methoxy)quinoline; m.p. 176°–178° C. (dec.); NMR: 1.53(t,3H), 3.08(q,2H), 5.29(s,2H), 6.86(s,1H), 7.02–7.10(m,6H), 7.32–7.48(m,14H), 7.52–7.70(m,3H), 8.08–8.18(m,3H); ¹³C NMR (benzylic CH₂) 70.01;

(29): 8-Chloro-2-ethyl-4-([2'-(2-triphenylmethyl-2H-tetrazol-5-yl)biphenyl-4-yl]methoxy)quinoline; m.p. 156°–158° C. (dec.); NMR: 1.42(t,3H), 3.05(q,2H), 5.16(s,2H), 6.8(s,1H), 6.87–6.98(m,6H), 7.15–7.33(m,14H), 7.38–7.55(m,3H), 7.78(dd,1H), 7.95–8.06(m,2H).

Using an analogous procedure to that described in *Org. Syn.*, 1955, Coll. Vol. III, pages 374 and 593, the following quinolones of formula IV were obtained in yields of 20–60%:—

2-Ethyl-6-trifluoromethyl-4-quinolone, m.p. 288°–289° C.;
2-Ethyl-8-trifluoromethyl-4-quinolone, m.p. 162°–163° C.;
5-Cyano-2-ethyl-4-quinolone, m.p.250° C. (dec.);
7-Cyano-2-ethyl-4-quinolone, (isolated as a 70:30 mixture of 7-CN and 5-CN isomers);
2-Ethyl-6-methoxy-4-quinolone, m.p. 210°–212° C.;
2-Ethyl-7-methoxy-4-quinolone, (isolated as an 80:20 mixture of 7-OMe and 5-OMe isomers);
2-Ethyl-8-methoxy-4-quinolone, m.p. 196°–198° C.;
2-Ethyl-5,7-dimethoxy-4-quinolone, m.p. 242°–244° C.;
2-Ethyl-5,8-dimethoxy-4-quinolone, m.p. 196°–198° C.;
2-Ethyl-6,7-dimethoxy-4-quinolone, m.p. 284°–287° C.;
2-Ethyl-5,6,7-trimethoxy-4-quinolone, m.p. 226°–228° C.;
Methyl 2-ethyl-4-hydroxyquinol-6-ylcarboxylate, 245° C. (dec.);
2-Ethyl-5-methyl-4-quinolone, m.p. 264°–266° C.*;
2-Ethyl-7-methyl-4-quinolone, m.p. 242°–244° C.*;
2-Ethyl-6,8-dimethyl-4-quinolone, m.p. 264°–266° C.; and
8-Chloro-2-ethyl-4-quinolone, m.p. 183°–184° C.
7-chloro-2-ethyl-4-quinolone (isolated as a 43.5:56.5) mixture of 7-Cl and 5-Cl isomers).

[*Note: these compounds were separated by flash chromatography on silica, eluting with methanol/dichloromethane (1:9 v/v) as eluant.]

2,6-Dimethyl-4-quinolone and 2,8-dimethyl-4-quinolone were obtained as described in *Ann. Chem.*, 1982, 1656–1676.

6-Chloro-2-methyl-4-quinolone was obtained as described in *Synthesis*, 1987, 482–3.

EXAMPLE 30

2M Aqueous sodium hydroxide solution (3.8 ml) was added to a solution of 6-carbomethoxy-2-ethyl-4-[(2'-(2-triphenylmethyl-2H-tetrazol-5-yl)biphenyl-4-yl)methoxy]quinoline in methanol (10 ml) and dioxane (15 ml). The solution was heated to reflux for 1 hour, cooled, and the solvent removed by evaporation. Water (40 ml) was added and the solution extracted with ethyl acetate (40 ml). The aqueous phase was acidified with concentrated hydrochloric acid (2 ml) and the resulting suspension dissolved in dioxane (20 ml). The solution was stirred for 1 hour then evaporated to a yellow gum. Crystallisation from methanol gave 6-carboxy-2-ethyl-4-[(2'-(1H-tetrazol-5-yl)biphenyl-4-yl)methoxy]quinoline hydrochloride (0.24 g) as a white powder, m.p. 161°–164° C.; NMR (d₆-DMSO): 1.45(t,3H), 3.24(q,2H), 5.68(s,2H), 7.24(d,2H), 7.53–7.76(m,7H), 8.47(d,2H), 8.77(d,1H); mass spectrum (-ve FAB, DMSO/GLY): 450 (M-H)⁻; microanalysis, found: C,61.3; H,4.9; N,13.3; H₂O,1.7%; C₂₆H₂₁N₅O₃.HCl.MeOH.0.5H₂O requires C,61.3; H,5.1; N,13.2; H₂O,1.7%.

EXAMPLE 31

Using an analogous procedure to that described in Example 7, but starting from 2-ethyl-6-(tert-butyldimethylsilyloxy)-4-([2'-(2-triphenylmethyl-2H-tetrazol-5-yl)biphenyl-4-yl]methoxy)quinoline, itself isolated as a foam [NMR: 0.25(s,6H), 1.02(s,9H), 1.38(t,3H), 2.94(q,2H), 5.20(s,2H), 6.68(s,1H), 6.88–6.98(m,6H), 7.17–7.34(m,14H), 7.40–7.60(m,4H), 7.89–8.00(m,2H); ¹³C NMR: (benzylic CH₂) 69.52] starting from 2-ethyl-6-(tert-butyldimethylsilyloxy)-4-quinolone, there was obtained 2-ethyl-6-hydroxy-4-[(2'-(1H-tetrazol-5-yl)biphenyl-4-yl)methoxy]quinoline hydrochloride, m.p. 189°–191° C.; NMR (d₆-DMSO): 1.42(t,3H), 3.14(q,2H), 5.61(s,2H), 7.22(d,2H), 7.49–7.72(m,9H), 8.20(d,1H); mass spectrum (-ve FAB, DMSO/GLY): 422 (M-H)⁻; microanalysis, found: C,62.7; H,4.8; N,14.4; H₂O,4.4%; C₂₅H₂₁N₅O₂.HCl.H₂O requires C,62.8; H,4.8; N,14.6; H₂O,3.8%.

EXAMPLES 32–54

Using an analogous procedure to that described in Example 7, but starting from the appropriate triphenylmethyl tetrazole (III), the following compounds of formula I were obtained in yields of 70–90%:—

(Example 32): 2-Ethyl-6-methylthio-4-[(2'-(1H-tetrazol-5-yl)biphenyl-4-yl)methoxy]quinoline hydrochloride, m.p. 156°–158° C.; NMR (d₆-DMSO): 1.40(t,3H), 2.62(s,3H), 3.17(q,2H), 5.66(s,2H), 7.20(d,2H), 7.51–7.70(m,7H), 7.90–7.95(m,2H), 8.25(d,1H); mass spectrum (-ve FAB, DMSO/GLY): 452 (M-H)⁻; microanalysis, found: C,63.2; H,4.8; N,13.7%; C₂₆H₂₃N₅OS.HCl.0.25.H₂O requires C,63.2; H,4.8; N,14.2%;

(Example 33): 2Ethyl-7-hydroxymethyl-4-[(2'-(1H-tetrazol-5-yl)biphenyl-4-yl)methoxy]quinoline hydrochloride, m.p. 228°–230° C.; NMR (d₆-DMSO): 1.41(t,3H), 3.15(q,2H), 5.06(s,2H), 5.62(s,2H), 7.20(d,2H), 7.55(d,2H), 7.56–7.62(m,3H), 7.65–7.72(m,2H), 7.99(d,2H), 8.12–8.20(m,1H); mass spectrum (-ve FAB, DMSO/GLY): 436 (M-H)⁻; microanalysis, found: C,65.7; H,5.1; N,14.8%; C₂₆H₂₃N₅O₂.HCl requires C,65.9; H,5.1; N,14.8%;

(Example 34): 2-Ethyl-6-methylsulphonyl-4-[(2'-(1H-tetrazol-5-yl)biphenyl-4-yl)methoxy]quinoline hydrochloride, m.p 149°–151° C. NMR (d$_6$-DMSO): 1.40(t,3H), 3.11(q,2H), 3.30(s,3H), 5.59(s,2H), 7.20(d,2H), 7.53–7.70(m,7H), 8.20(d,1H), 8.33(dd,1H), 8.67(d,1H); mass spectrum (-ve FAB, DMSO/GLY): 484 (M-H)$^-$; microanalysis, found: C,58.3; H,5.0; N,12.2%; C$_{26}$H$_{23}$N$_5$O$_3$S.HCl.H$_2$O requires C,57.8; H,4.9; N,13.0%;

(Example 35): 2-Ethyl-6,7-methylenedioxy-4-[(2'-(1H-tetrazol-5-yl)biphenyl-4-yl)methoxy]quinoline hydrochloride, m.p. 174°–175° C.; NMR (d$_6$-DMSO): 1.40(t,3H), 3.11(q,2H), 5.62(s,2H), 6.35(s,2H), 7.19(d,2H), 7.45–7.76(m,9H); mass spectrum (-ve FAB, DMSO/GLY): 450 (M-H)$^-$; microanalysis, found: C,61.6; H,4.8; N,13.2; H$_2$O,4.3%; C$_{26}$H$_{21}$N$_5$O$_3$.HCl.1.2-H$_2$O requires C,61.3; H,4.8; N,13.7; H$_2$O,4.2%;

(Example 36): 2-Ethyl-6-(2-fluoroethoxy)-4-[(2'-(1H-tetrazol-5-yl)biphenyl-4-yl)methoxy]quinoline hydrochloride, m.p. 161°–163° C.; NMR (d$_6$-DMSO): 1.40(t,3H), 3.12(q,2H), 4.32–4.55(m,2H), 4.66–4.98(m,2H), 5.64(s,2H), 7.20(d,2H), 7.50–7.81(m,9H), 8.24(d,1H); mass spectrum (-ve FAB, DMSO/GLY): 468 (M-H)$^-$; microanalysis, found: C,63.1; H,4.9; N,12.9; H$_2$O,1.7%; C$_{27}$H$_{24}$N$_5$O$_2$F.HCl.0.5H$_2$O requires C,63.0; H,4.8; N,13.6; H$_2$O, 1.8%;

(Example 37): 7-Carboethoxy-2-ethyl-4-[(2'-(1H-tetrazol-5-yl)biphenyl-4-yl)methoxy]quinoline hydrochloride, m.p. 226°–228° C.; NMR (CD$_3$CN/CF$_3$CO$_2$H): 1.55(t,3H), 1.62(t,3H), 3.31(q,2H), 4.60(q,2H), 5.75(s,2H), 7.42(d,2H), 7.52(s,1H), 7.70(d,2H), 7.73–7.78(m,2H), 7.85–7.91(m,2H), 8.44(dd,1H), 8.60(d,1H), 8.78(d,1H); mass spectrum (-ve FAB, DMSO/GLY): 479 (M-H)$^-$; microanalysis, found: C,64.7; H,5.0; N,13.4; H$_2$O,0.4%; C$_{28}$H$_{25}$N$_5$O$_3$.HCl.0.1-H$_2$O requires C,64.9; H,5.1; N,13.5; H$_2$O,0.3%;

(Example 38): 2-Ethyl-6-(2,2,2-trifluoroethoxy)-4-[(2'-(1H-tetrazol-5-yl)biphenyl-4-yl)methoxy]quinoline hydrochloride, m.p. 140°–141° C.; NMR (d$_6$-DMSO): 1.41(t,3H), 3.14(q,2H), 5.03(q,2H), 5.68(s,2H), 7.20(s,2H), 7.52–7.75(m,8H), 7.85(dd,1H), 8.28(d,1H), mass spectrum (-ve FAB, DMSO/GLY): 504 (M-H)$^-$; microanalysis, found: C,58.0; H,4.7; N,12.4; H$_2$O,2.6%; C$_{27}$H$_{22}$N$_5$O$_2$F$_3$.HCl.H$_2$O requires C,57.9; H,4.3; N,12.5; H$_2$O,3.2%;

(Example 39): 6-Carboxamido-2-ethyl-4-[(2'-(1H-tetrazol-5-yl)biphenyl- 4-yl)methoxy]quinoline hydrochloride, m.p. 178°–180° C.; NMR (d$_6$-DMSO): 1.44(t,3H), 3.21(q,2H), 5.69(s,2H), 7.22(d,2H), 7.57–7.75(m,6H), 8.36(d,1H), 8.46(dd,2H), 8.76(d,1H); mass spectrum (+ve FAB, DMSO/GLY): 451 (M+H)+; microanalysis, found: C,62.4; H,5.1; N,16.1; H$_2$O,1.7%; C$_{26}$H$_{22}$N$_6$O$_2$.HCl.0.25H$_2$O.0.4CH$_3$OH requires C,62.3; H,5.0; N,16.5; H$_2$O,1.8%;

(Example 40): 2-Ethyl-6-trifluoromethoxy-4-[(2'-(1H-tetrazol-5-yl)biphenyl-4-yl)methoxy]quinoline hydrochloride, m.p. 180°–182° C.; NMR (d$_6$-DMSO): 1.43(t,3H), 3.18(q,2H), 5.65(s,2H), 7.20(d,2H), 7.52–7.73(m,7H), 8.03–8.15(m,2H), 8.41(d,1H); mass spectrum (-ve FAB, DMSO/GLY): 490 (M-H)$^-$; microanalysis, found: C,59.0; H,3.6; N,13.2%; C$_{26}$H$_{20}$N$_5$O$_2$F$_3$.HCl requires C,59.1; H,4.0; N,13.3%;

(Example 41): 6-Cyano-2-ethyl-4-[(2'-(1H-tetrazol-5-yl)biphenyl-4-yl)methoxy]quinoline hydrochloride, m.p. 153°–155° C.; NMR (d$_6$-DMSO): 1.41(t,3H), 3.15(q,2H), 5.62(s,2H), 7.20(d,2H), 7.53–7.75(m,7H), 8.22–8.39(m,2H), 8.79(s,1H); mass spectrum (+ve FAB, DMSO/GLY): 433 (M+H)+; microanalysis, found: C,66.9; H,4.3; N,17.6%; C$_{26}$H$_{20}$N$_6$O.HCl requires C,66.6; H,4.5; N,17.9%;

(Example 42): 2-Ethyl-6-formyl-4-[(2'-(1H-tetrazol-5-yl)biphenyl-4-yl)methoxy]quinoline hydrochloride, m.p. 142°–144° C.; NMR (d$_6$-DMSO): 1.45(t,3H), 3.20(q,2H), 5.70(s,2H), 7.22(d,2H), 7.52–7.75(m,7H), 8.34–8.49(m,2H), 8.85(s,1H), 10.22(s,1H); mass spectrum (+ve FAB, DMSO/NBA): 436 (M+H)+; microanalysis, found: C,65.0; H,4.6; N,14.4%; C$_{26}$H$_{21}$N$_5$O$_2$.HCl.0.5H$_2$O requires C,64.9; H,4.8; N,14.6%;

(Example 43): 6-Dimethylamino-2-ethyl-4-[(2'-(1H-tetrazol-5-yl)biphenyl-4-yl)methoxy]quinoline dihydrochloride, m.p. 206°–209° C.; NMR (d$_6$-DMSO): 1.40(t,3H), 3.07(s,6H), 3.12(q,2H), 5.63(s,2H), 7.05(d,1H), 7.21(d,2H), 7.45(s,1H), 7.51(s,1H), 7.55–7.65(m,3H), 7.66–7.75(m,3H), 8.23(d,1H); mass spectrum (+ve FAB, DMSO/NBA): 451 (M+H)+; microanalysis, found: C,61.8; H,5.4; N,16.0; Cl,13.2%; C$_{27}$H$_{26}$N$_6$O.2HCl requires C,61.9; H,5.4; N,16.1; Cl,13.6%;

(Example 44): 2-Ethyl-6-nitro-4-[(2'-(1H-tetrazol-5-yl)biphenyl-4-yl)methoxy]quinoline hydrochloride, m.p. 149°–152° C.; NMR (d$_6$-DMSO): 1.45(t,3H), 3.18(q,2H), 5.66(s,2H), 7.22(d,2H), 7.54–7.75(m,7H), 8.45(d,1H), 8.68(dd,1H), 8.95(d,1H); mass spectrum (+ve FAB, DMSO/NBA): 453 (M+H)+; microanalysis, found: C,59.3; H,4.5; N,16.8; H$_2$O, 3.9%; C$_{25}$H$_{20}$N$_6$O$_3$.HCl.H$_2$O requires C,59.2; H,4.5; N,16.6; H$_2$O, 3.6%;

(Example 45): 6-Cyano-2-methyl-4-[(2'-(1H-tetrazol-5-yl)biphenyl-4-yl)methoxy]quinoline hydrochloride, m.p. 280°–282° C.; NMR (d$_6$-DMSO): 2.90(s,3H), 5.63(s,2H), 7.21(d,2H), 7.57–7.79(m,8H), 8.25–8.41(m,2H), 8.79(s,1H); mass spectrum (-ve FAB, DMSO/GLY): 417 (M-H)$^-$; microanalysis, found: C,66.0; H,4.5; N,17.8%; C$_{25}$H$_{18}$N$_6$O.HCl requires C,66.0; H,4.2; N,18.5%;

(Example 46): 2-Ethyl-6-fluoro-4-[(2'-(1H-tetrazol-5-yl)biphenyl-4-yl)methoxy]quinoline hydrochloride, m.p. 185°–186° C.; NMR (d$_6$-DMSO): 1.44(t,3H), 3.20(q,2H), 5.67(s,2H), 7.20(d,2H), 7.50–7.78(m,7H), 7.93–8.08(m,2H), 8.36–8.49(m,1H); mass spectrum (-ve FAB, DMSO/GLY): 424 (M-H)$^-$; microanalysis, found: C,64.7; H,4.4; N,14.8%; C$_{25}$H$_{20}$N$_5$FO.HCl requires: C,65.0; H,4.6; N,15.2%;

(Example 47): 2-Ethyl-6-isopropoxy-4-[(2'-[(2'-(1H-tetrazol-5-yl)biphenyl-4-yl)methoxy]quinoline hydrochloride, m.p. 177°–180° C. (dec); NMR (d$_6$-DMSO): 1.36(d,6H), 1.4(t,3H), 3.16(q,2H), 4.83(m, 1H), 5.66(s,2H), 7.20(d,2H), 7.48–7.65(m,6H), 7.65–7.75(m,3H), 8.28(d,1H); mass spectrum (-ve FAB, DMSO/GLY): 464 (M-H)$^-$; microanalysis, found: C,66.2; H,6.1; N,13.8; H$_2$O,0.2%; C$_{28}$H$_{27}$N$_5$O$_2$.HCl.0.1(CH$_3$)$_2$CHOH.0.25H$_2$O requires C,66.3; H,5.7; N,13.7; H$_2$O,0.9%;

(Example 48): 5-Chloro-2-ethyl-4-[(2'-(1H-tetrazol-5-yl)biphenyl-4-yl)methoxy]quinoline hydrochloride, m.p. 189°–190° C. (dec); NMR (d$_6$-DMSO): 1.41(t,3H), 3.14(q,2H), 5.63(s,2H), 7.19(d,2H), 7.50–7.63(m,5H), 7.63–7.74(m,2H), 7.84(d,1H), 7.94(t,1H), 8.28(d,1H); mass spectrum (-ve FAB, DMSO/GLY): 440 (M-H)$^-$; microanalysis, found: C,62.8; H,4.2; N,14.7%; C$_{25}$H$_{20}$N$_5$ClO.HCl requires C,62.8; H,4.4; N,14.6%;

(Example 49): 2-Trifluoromethyl-4-[(2'-(1H-tetrazol-5-yl)biphenyl-4-yl)methoxy]quinoline, m.p. 187°–190° C. (dec); NMR (d$_6$-DMSO): 5.53(s,2H), 7.20(d,2H), 7.50–7.80(m,8H), 7.90(dt,1H), 8.12(d,1H), 8.28(dd,1H), 13.0(brs,1H); mass spectrum (-ve FAB, DMSO/GLY): 446 (M-H)$^-$; microanalysis, found: C,64.3; H,3.3; N,15.5%; $C_{24}H_{16}N_5F_3O$ requires C,64.4; H,3.6; N,15.7%;

(Example 50): 2-Methoxymethyl-4-[(2'-(1H-tetrazol-5-yl)biphenyl-4-yl)methoxy]quinoline hydrochloride, m.p. 169°–171° C.; NMR (d$_6$-DMSO): 3.50(s,3H), 4.98(s,2H), 5.67(s,2H), 7.22(d,2H), 7.54–7.74(m,7H), 7.84(t,1H), 8.08(t,1H), 8.32–8.38(m,2H); mass spectrum (-ve FAB, DMSO/GLY): 422 (M-H)$^-$; microanalysis, found; C,65.2; H,4.8; N,15.2%; $C_{25}H_{21}N_5O_2$.HCl requires C,65.3; H,4.8; N,15.2%;

(Example 51): 2-Ethoxymethyl-4-(2'(1H-tetrazol-5-yl)biphenyl-4-yl)methoxy]quinoline hydrochloride, m.p. 164°–166° C.; NMR (d$_6$-DMSO): 1.25(t,3H), 3.68(q,2H), 4.99(s,2H), 5.68(s,2H), 7.21(d,2H), 7.54–7.72(m,7H), 7.84(t,1H), 8.08(t,1H), 8.34(d,2H); mass spectrum (-ve FAB, DMSO/GLY): 436(M-H)$^-$; microanalysis, found; C,65.6; H,5.2; N,14.4%; $C_{26}H_{23}N_5O_2$.HCl requires C,65.9; H,5.1; N,14.8%;

(Example 52): 2,3-Dimethyl-4-[(2'-(1H-tetrazol-5-yl)biphenyl-4-yl)methoxy]quinoline hydrochloride, m.p. 155°–156° C. (dec); NMR (d$_6$-DMSO): 2.35(s,3H), 2.95(s,3H), 5.38(s,2H), 7.16(d,2H), 7.47(d,2H), 7.53–7.76(m,4H), 7.85(t,1H), 8.05(dt,1H), 8.19(d,1H), 8.38(d,1H); mass spectrum (+ve FAB, DMSO/NBA): 408 (M+H)+; microanalysis, found: C,66.8; H,4.9; N,15.3%; $C_{25}H_{21}N_5O$.HCl.0.25CH$_3$OH requires C,67.1; H,5.1; N,15.5%;

(Example 53): 2-(3,3,3-Trifluoropropyl)-4-[(2'-(1H-tetrazol-5-yl)biphenyl-4-yl)methoxy]quinoline hydrochloride, m.p. 204°–206° C. (dec); NMR (d$_6$-DMSO): 2.92–3.14(m,2H), 3.40–3.51(m,2H), 5.64(s,2H), 7.21(d,2H), 7.50–7.64(m,4H), 7.65–7.87(m,4H), 8.08(t,1H), 8.25–8.35(m,2H); mass spectrum (+re FAB, DMSO/NBA): 476 (M+H)+; microanalysis, found: C,60.8; H,3.9; N,13.7%; $C_{26}H_{20}N_5F_3O$.HCl requires C,61.0; H,4.1; N,13.7%;

(Example 54): 2-Hydroxymethyl-4-[(2'-(1H-tetrazol-5-yl)biphenyl-4-yl)methoxy]quinoline hydrochloride, m.p. 199°–201° C. (dec); NMR (d$_6$-DMSO): 5.07(s,2H), 5.66(s,2H), 7.22(d,2H), 7.53–7.63(m,4H), 7.65–7.75(m,3H), 7.83(t,1H), 8.09(t,1H), 8.32(d,1H), 8.39(d,1H); mass spectrum (-ve FAB, DMSO/GLY): 408 (M-H)$^-$; microanalysis, found: C,64.2; H,4.7; N,15.5%; $C_{24}H_{19}N_5O_2$.HCl requires C,64.6; H,4.5; N,15.7%;

The necessary starting materials of formula III used in Examples 32–53 were obtained in yields of 20–70% using an analogous procedure to that described in Example 7 but starting from the appropriate quinolones of formula IV. The compounds of formula III had the following properties:—

(32): 2-Ethyl-6-methylthio-4-([2'-(2-triphenylmethyl-2H-tetrazol- 5-yl)biphenyl-4-y]methoxy)quinoline, m.p. 164°–166° C.; NMR: 1.37(t,3H), 2.50(s,3H), 2.92(q,2H), 5.19(s,2H), 6.70(s,1H), 6.91–6.95(m,6H), 7.19–7.34(m,14H), 7.44–7.60(m,4H), 7.89–7.99(m,2H); $^{13}$C NMR: (benzylic CH$_2$) 69.82;

(33): 2-Ethyl-7-hydroxymethyl-4-([2'-(2-triphenylmethyl-2H-tetrazol-5-yl)biphenyl-4-yl]methoxy)quinoline, m.p. 99°–102° C.; NMR(d$_6$-DMSO): 1.29(t,3H), 2.82(q,2H), 5.10(s,2H), 5.31(s,2H), 6.84–6.93(m,6H), 7.02(s,1H), 7.15(d,2H), 7.27–7.38(m,9H), 7.44(d,2H), 7.48–7.83(m,7H);

(34): 2-Ethyl-6-methylsulphonyl-4-([2'-(2-triphenylmethyl-2H-tetrazol-5-yl)biphenyl-4-yl]methoxy)quinoline, isolated as a foam; NMR: 1.19(t,3H), 2.76(q,2H), 2.89(s,3H), 5.03(s,2H), 6.61(s,1H), 6.72–6.77(m,6H), 7.00–7.12(m,13H), 7.22–7.35(m,3H), 7.74–7.78(m,1H), 7.85–7.98(m,2H), 8.67(s,1H); $^{13}$C NMR: (benzylic CH$_2$) 70.52;

(35): 2-Ethyl-6,7-methylenedioxy-4-([2'-(2-triphenylmethyl-2H-tetrazol-5-yl)biphenyl-4-yl]methoxy)quinoline, isolated as a foam; NMR 1.38(t,3H), 2.90(q,2H), 5.15(s,2H), 6.09(s,2H), 6.65(s,1H), 6.88–6.98(m,6H), 7.16–7.55(m,19H), 7.96–8.03(m,1H); $^{13}$C NMR: (benzylic CH$_2$) 69.75;

(36): 2-Ethyl-6-(2-fluoroethoxy)-4-([2'-(2-triphenylmethyl-2H-tetrazol-5-yl)biphenyl-4-yl]methoxy)quinoline, m.p. 173°–175° C.; NMR: 1.30(t,3H), 2.84(q,2H), 4.03–4.19(m,2H), 4.51–4.74(m,2H), 5.11(s,2H), 6.64(s,1H), 6.85–6.90(m,6H), 7.12–7.46(m,18H), 7.85–7.89(m,2H); $^{13}$C NMR: (benzylic CH$_2$) 69.93;

(37): 7-Carboethoxy-2-ethyl-4-([2'-(2-triphenylmethyl-2H-tetrazol-5-yl)biphenyl-4-yl]methoxy)quinoline, m.p. 160°–163° C.; NMR (d$_6$-DMSO): 1.33(t,3H), 1.38(t,3H), 2.92(q,2H), 4.38(q,2H), 5.35(s,2H), 6.84–6.89(m,6H), 7.16(d,2H), 7.21(s,1H), 7.29–7.31(m,9H), 7.42(d,2H), 7.52–7.65(m,3H), 7.83–7.89(m,2H), 8.10(d,1H), 8.46(d,1H);

(38): 2-Ethyl-6-(2,2,2-trifluoroethoxy)-4-([2'-(2-triphenylmethyl-2H-tetrazol-5-yl)biphenyl-4-yl]methoxy)quinoline, m.p. 147°–149° C.; NMR: 1.40(t,3H), 2.95(q,2H), 4.38(q,2H), 5.21(s,2H), 6.73(s,1H), 6.92–7.00(m,6H), 7.21–7.55(m,18H), 7.93–8.00(m,2H); 13 NMR: (benzylic CH$_2$) 70.00;

(39): 6-Carboxamido-2-ethyl-4-([2'-(2-triphenylmethyl-2H-tetrazol-5-yl)biphenyl-4-yl]methoxy)quinoline, isolated as a foam; NMR: 1.31(t,3H), 2.87(q,2H), 5.38(s,2H), 6.82–6.89(m,6H), 7.13(d,2H), 7.31–7.34(m,9H), 7.45(d,2H), 7.54–7.63(m,3H), 7.80–7.94(m,3H), 8.14(dd,1H), 8.70(d,1H);

(40): 2-Ethyl-6-trifluoromethoxy-4-([2'-(2-triphenylmethyl-2H-tetrazol-5-yl)biphenyl-4-yl]methoxy)quinoline, m.p. 144°–146° C.; NMR: 1.38(t,3H), 2.95(q,2H), 5.18(s,2H), 6.75(s,1H), 6.90–6.97(m,6H), 7.20–7.32(m,13H), 7.39–7.55(m,4H), 7.95–8.05(m,3H); $^{13}$C NMR: (benzylic CH$_2$) 70.22;

(41): 6-Cyano-2-ethyl-4-([2'-(2-triphenylmethyl-2H-tetrazol-5-yl)biphenyl-4-yl]methoxy)quinoline, m.p. 178°–179° C.; NMR (d$_6$-DMSO): 1.33(t,3H), 2.92(q,2H), 5.36(s,2H), 6.80–6.90(m,6H), 7.16–8.02(m,20H), 8.42(s,1H);

(42): 2-Ethyl-6-formyl-4-([2'-(2-triphenylmethyl-2H-tetrazol-5-yl)biphenyl-4-yl]methoxy)quinoline, m.p. 164°–166° C.; NMR (d$_6$-DMSO): 1.34(t,3H), 2.92(q,2H), 5.40(s,2H), 6.85–6.91(m,6H), 7.17–7.33(m,13H), 7.46–7.66(m,4H), 7.82(dd,1H), 8.05(dq,2H), 8.59(d,1H), 9.91(s,1H);

(43): 6-Dimethylamino-2-ethyl-4-([2'-2-triphenylmethyl-2H-tetrazol-5-yl)biphenyl-4-yl]methoxy)quinoline, isolated as a foam; NMR (d$_6$-DMSO): 1.28(t,3H), 2.83(q,2H), 2.94(s,6H), 5.35(s,2H), 6.82–6.94(m,6H), 6.98(s,1H), 7.08(d,1H), 7.15(d,2H), 7.27–7.40(m,9H), 7.41–7.70(m,6H), 7.72–7.84(m,2H);

(44): 2-Ethyl-6-nitro-4-([2'-(2-triphenylmethyl-2H-tetrazol-5-yl)biphenyl-4-yl]methoxy)quinoline, isolated as a foam; NMR (d$_6$-DMSO): 1.34(t,3H), 2.94(q,2H), 5.42(s,2H), 6.84–6.89(m,6H), 7.18(d,2H), 7.30–7.36(m,9H), 7.42–7.65(m,6H), 7.84(d,1H), 8.07(d,1H), 8.41(dd,1H), 8.88(d,1H);

(45): 6-Cyano-2-methyl-4-([2'-(2-triphenylmethyl-2H-tetrazol-5-yl)biphenyl-4-yl]methoxy)quinoline, m.p. 188° C. (dec.); NMR (d$_6$-DMSO): 2.65(s,3H), 5.35(s,2H), 6.82–6.89(m,6H), 7.16–7.34(m,13H), 7.43–7.67(m,4H), 7.86(dd,1H), 7.98(s,2H), 8.42(s,1H);

(46): 2-Ethyl-6-fluoro-4-([2'-(2-triphenylmethyl-2H-tetrazol-5-yl)biphenyl-4-yl]methoxy)quinoline; m.p. 183°–184° C.; NMR: 1.40(t,3H), 2.95(q,2H), 5.18(s,2H), 6.75(s,1H), 6.87–6.98(m,6H), 7.17–7.35(m,13H), 7.36–7.58(m,4H), 7.70(dd,1H), 7.93–8.05(m,2H); microanalysis, found: C,78.8; H,5.1; N,10.5%; $C_{44}H_{34}N_5FO$ requires C,79.1; H,5.1; N,10.5%;

(47): 2-Ethyl-6-isopropoxy-4-([2'-(2-triphenylmethyl-2H-tetrazol-5-yl)biphenyl-4-yl]methoxy)quinoline, isolated as a foam; NMR: 1.35(d,6H), 1.38(t,3H), 2.90(q,2H), 4.64(m,1H), 5.19(s,2H), 6.69(s,1H), 6.90–6.98(m,6H), 7.15–7.35(m,14H), 7.38–7.55(m,4H), 7.92(d,1H), 7.95(dd,1H);

(48): 5-Chloro-2-ethyl-4-([2'-(triphenylmethyl-2H-tetrazol-5-yl)biphenyl-4-yl]methoxy)quinoline; m.p. 180°–181° C. (dec.); NMR ($d_6$-DMSO): 1.3(t,3H), 2.85(q,2H), 5.35(s,2H), 6.80–6.92(m,6H), 7.13(t,3H), 7.23–7.37(m,9H), 7.40–7.67(m,7H), 7.74–7.88(m,2H);

(49): 2-Trifluoromethyl-4-([2'-(2-triphenylmethyl-2H-tetrazol-5-yl)biphenyl-4-yl]methoxy)quinoline, isolated as an amorphous solid; NMR ($d_6$-DMSO): 5.48(s,2H), 6.8–6.94(m,6H), 7.19(d,2H), 7.24–7.38(m,9H), 7.4–7.69(m,7H), 7.8–7.94(m,2H), 8.07–8.17(m,2H); $^{13}C$ NMR: (benzylic $CH_2$) 70.45;

(50): 2-Methoxymethyl-4-([2'-(2-triphenylmethyl-2H-tetrazol-5-yl)biphenyl-4-yl]methoxy)quinoline; m.p 174°–176° C.; NMR: 3.52(s,3H), 4.73(s,2H), 5.19(s,2H), 6.89–6.94(m,6H), 7.06(s,1H), 7.18–7.30(m,13H), 7.30–7.53(m,4H), 7.69(dt,1H), 7.98(m,2H), 8.14(dd,1H); microanalysis, found: C,78.7; H,5.2; N,10.4%; $C_{44}H_{35}N_5O_2 \cdot 0.25H_2O$ requires C,78.9; H,5.3; N,10.5%;

(51): 2-Ethoxymethyl-4-([2'-(2-triphenylmethyl-2H-tetrazol-5-yl)biphenyl-4-yl]methoxy)quinoline; m.p 156°–158° C.; NMR: 1.29(t,3H), 3.66(q,2H), 4.77(s,2H), 5.20(s,2H), 6.90–6.94(m,6H), 7.09(s,1H), 7.18–7.29(m,13H), 7.30–7.53(m,4H), 7.68(dt,1H), 7.96–8.03(m,2H), 8.14(dd,1H); microanalysis, found: C,79.0; H,5.5; N,10.3%; $C_{45}H_{37}N_5O_2$ requires C,79.5; H,5.5; N,10.3%;

(52): 2,3-Dimethyl-4-([2'-(2-triphenylmethyl-2H-tetrazol-5-yl)biphenyl-4-yl]methoxy)quinoline; m.p 170°–172° C.; NMR: 2.37(s,3H), 2.73(s,3H), 4.95(s,2H), 6.90–6.99(m,6H), 7.18–7.35(m,13H), 7.37–7.58(m,4H), 7.64(dt,1H), 7.95–8.07(m,3H);

(53): 2-(3,3,3-Trifluoropropyl)-4-([2'-(2-triphenylmethyl-2H-tetrazol-5-yl)biphenyl-4-yl]methoxy)quinoline, isolated as an amorphous solid, m.p 182°–184° C.; NMR ($d_6$-DMSO): 2.7–3.0(m,2H), 3.05–3.20(m,2H), 5.32(s,2H), 6.80–6.90(m,6H), 7.12–7.65(m,18H), 7.70(dt,1H), 7.87(dt,2H), 8.03(d,1H);

The starting material used in Example 54 was obtained as follows:—

(i) Using an analogous procedure to that described in Example 7 but starting from the appropriate quinolone of formula IV, there was thus obtained 2-ethoxycarbonyl-4-([2'-(2-triphenylmethyl-2H-tetrazol- 5-yl)biphenyl-4-yl]methoxy)quinoline; m.p. 146°–147° C. (dec.); NMR: 1.51(t,3H), 4.57(q,2H), 5.23(s,2H), 6.89–6.94(m,6H), 7.18–7.30(m,13H), 7.40–7.53(m,4H), 7.68(s,1H), 7.75(dt,1H), 8.0(m,1H), 8.17(d,1H), 8.26(d,1H).

(ii) Lithium borohydride (11 mg) was added to a solution of 2-ethoxycarbonyl-4-([2'-(2-triphenylmethyl-2H-tetrazol-5-yl)biphenyl-4-yl]methoxy)quinoline (346 mg) in tetrahydrofuran (4 ml) and the mixture stirred for 18 hours. Water (20 ml) was added to the mixture and a white solid precipitated. The solid was collected by filtration, dissolved in ethyl acetate and the solution dried ($MgSO_4$). The solvent was removed by evaporation and the residue crystallised from ethyl acetate/hexane to give 2-hydroxymethy-4-([2'-(2-triphenylmethyl-2H-tetrazol-5-yl)biphenyl-4-yl]methoxy)quinoline (213 mg), as a white crystalline solid, m.p. 183°–185° C. (dec.); NMR: 4.85(s,2H), 5.18(s,2H), 6.70(s,1H), 6.85–6.98(m,6H), 7.15–7.35(m,13H), 7.35–7.58(m,4H), 7.70(dt,1H), 7.95–8.08(m,2H), 8.15(d,1H); microanalysis, found: C,78.7; H,4.7; N,10.7%; $C_{43}H_{33}N_5O_2$ requires C,79.2; H,5.1; N,10.7%.

Using an analogous procedure to that described in Org. Syn., 1955, Coll. Vol. III, pages 374 and 593, the following quinolones used in Examples 31, 32, 35–47 and 49–54 may be obtained in yields of 20–60%:—

2-Ethyl-6-(tert-butyldimethylsilyloxy)-4-quinolone, m.p. 197°–198° C.;
2-Ethyl-6-methylthio-4-quinolone, m.p. 196°–199° C.;
2-Ethyl-6,7-methylenedioxy-4-quinolone, m.p. 250° C. (dec.);
2-Ethyl-6-(2-fluoroethoxy)-4-quinolone, m.p. 267°–269° C.;
7-Carboethoxy-2-ethyl-4-quinolone, m.p. 220°–223° C.;
2-Ethyl-6-(2,2,2-trifluoroethoxy)-4-quinolone, m.p. 260° C. (dec.);
6-Carboxamido-2-ethyl-4-quinolone, m.p. >300° C.;
2-Ethyl-6-trifluoromethoxy-4-quinolone, m.p. 258°–260° C.;
6-Cyano-2-ethyl-4-quinolone, m.p. 290° C. (dec.);
2-Ethyl-6-formyl-4-quinolone, m.p. 285° C. (dec.);
6-Dimethylamino-2-ethyl-4-quinolone, m.p. 237°–239° C.;
2-Ethyl-6-nitro-4-quinolone, m.p. >280° C.;
6-Cyano-2-methyl-4-quinolone, m.p. 297°–8° C.;
2-Ethyl-6-fluoro-4-quinolone, m.p. 243°–245° C.;
2-Ethyl-6-isopropoxy-4-quinolone, m.p. 174°–177° C.;
2-Trifluoromethyl-4-quinolone, m.p. 210°–212° C.;
2-Methoxymethyl-4-quinolone, m.p. 186°–188° C.;
2-Ethoxymethyl-4-quinolone, m.p. 146° C.;
2,3-Dimethyl-4-quinolone, m.p. >300° C.;
2-Ethoxycarbonyl-4-quinolone, m.p. 214°–215° C.;
2-(3,3,3-Trifluoropropyl)-4-quinolone, m.p. 240°–242° C.

2-Ethyl-7-hydroxymethyl-4-quinolone used in Example 33 was obtained as follows:—

Lithium aluminium hydride (0.6 g) was added to a solution of 7-carboethoxy-2-ethyl-4-quinolone (2.65 g) in THF (200 ml) and the resulting suspension stirred for 2 hours at ambient temperature. Water (100 ml) was slowly added, followed by ethyl acetate (100 ml). The suspension was filtered and washed with ethyl acetate (100 ml). The phases of the filtrate were separated and the aqueous layer re-extracted with ethyl acetate (100 ml). The combined organic phases were dried ($MgSO_4$) and evaporated to give a solid which on recrystallisation from ethyl acetate gave 2-ethyl-7-hydroxymethyl-4-quinolone as a white powder, m.p. 254°–257° C.

2-Ethyl-6-methylsulphonyl-4-quinolone used in Example 34 was obtained as follows:—

Oxone (920 mg) was added to a solution of 2-ethyl-6-methylthio-4-quinolone (220 mg) in methanol (10 ml) and water (1 ml). The suspension was stirred at ambient temperature for 1 hour then evaporated to give a yellow solid. Saturated sodium bicarbonate solution (10 ml) was added and the resulting precipitate collected by filtration and dried to give 2-ethyl-6-methylsulphonyl- 4-quinolone (150 mg) as a light yellow powder, m.p. 283° C.

5-Chloro-2-ethyl-4-quinolone used in Example 48 was obtained as follows:—

A mixture of 4-benzyloxy-5-chloro-2-ethyl quinoline (A) (1.8 g) and a solution of hydrogen bromide in acetic acid (45% w/v; 30 ml) was heated at 100° C. for 4 hours. The mixture was diluted with ice/water and basified to pH 9 with 5M aqueous sodium hydroxide solution, when a solid precipitated. The mixture containing the solid precipitate was extracted with ethyl acetate (50 ml), and the solid was then collected by filtration. The solid was purified by flash chromatography, eluting with methanol/dichloromethane (4:96 v/v) to give 5-chloro-2-ethyl-4-quinolone as a white solid, m.p. 236°–239° C.; NMR (d$_6$-DMSO): 1.25(t,3H), 2.58(q,2H), 5.89(s,1H), 7.2(dd,1H), 7.42–7.53(m,2H), 11.4(brs,1H); microanalysis, found: C,63.2; H,4.8; N,6.6%; C$_{11}$H$_{10}$NClO requires C,63.6; H,4.8; N,6.8%.

The starting material (A) was obtained as follows:—

Sodium hydride (60% dispersion in mineral oil; 1.95 g) was added to a stirred solution of a mixture of 7-chloro-2-ethyl-4-quinolone and 5-chloro-2-ethyl-4-quinolone (43.5:56.5, 10 g) in DMF (100 ml). The mixture was stirred until evolution of hydrogen had ceased and benzylbromide (8.25 g) was added. The mixture was stirred for 18 hours. The solvent was removed by evaporation and the residue partitioned between water (80 ml) and dichloromethane (2×100 ml). The organic layer was washed with saturated sodium chloride solution (50 ml) and dried (MgSO$_4$). The solvent was removed by evaporation and the resultant yellow oil was purified by flash chromatography, eluting with increasing concentration of ethyl acetate in dichloromethane. The product was eluted with ethyl acetate/dichloromethane (10:90 v/v) to give 4-benzyloxy-5-chloro-2-ethylquinoline as a white solid (2.6 g), m.p. 78°–80° C.; NMR: 1.39(t,3H), 2.94(q,2H), 5.38(s,2H), 6.72(s,1H), 7.30–7.55(m,6H), 8.0(d,1H), 8.13(d,1H).

EXAMPLE 55

A solution of 2-ethyl-4-[(2'-(2-tributylstannyl-2H-tetrazol-5-yl)biphenyl-4-yl)methoxy]quinoline in toluene (15 ml), prepared in situ by refluxing for 90 hours a mixture of 4'-[(2-ethylquinolin-4-yloxy)methyl]biphenyl-2-carbonitrile (0.9 g) and a solution of tributyltin azide in toluene (15 ml) [the latter prepared by reaction of tributyltin chloride (3.3 g) and sodium azide (1.13 g) in water (22.5 ml) at ambient temperature for 4 hours, followed by extraction with toluene and azeotropic removal of water from the extract to leave a volume of 15 ml], was added slowly over 1 hour to a solution of sodium nitrite (2.5 g) in water (10 ml) containing 12% w/v hydrochloric acid (10 ml), maintaining the temperature of the mixture below 5° C. A solution of sulphamic acid (1.43g) in water (10ml) was then added, maintaining the temperature below 5° C., and the mixture stirred for 1 hour. The resultant suspended semi-solid was collected by filtration and washed with water (3×10 ml), followed by toluene (10 ml). The semi-solid was then added to tetrahydrofuran (THF) (40 ml), which caused the product to dissolve and then crystallise as a white solid. After cooling for one hour the solid was collected by filtration, washed with THF (5 ml) and dried to give 2-ethyl-4-[(2'-(1H-tetrazol-5-yl)biphenyl-4-yl)methoxy]quinoline hydrochloride; m.p. 179°–180° C. (dec.); NMR (d$_6$-DMSO): 1.46(t,3H), 3.18(q,2H), 5.68(s,2H), 7.22(d,2H), 7.5–7.8(m,7H), 7.83(t,1H), 8.08(t,1H), 8.18(d,1H), 8.32(d,1H).

EXAMPLE 56

A mixture of 2-ethyl-4-quinolone (1.73 g), (prepared by a similar method to that described in Org. Syn., Coll. Vol. III, p.374 and p.593 from aniline and methyl propionylacetate), 4'-bromomethylbiphenyl-2-carbonitrile (A) (3.1 g) and solid potassium carbonate (1.81 g) in N-methylpyrrolidone (40 ml) were stirred for 36 hours under nitrogen. The mixture was then added dropwise to water (100 ml) at 15°–25° C. and stirred for 30 minutes. The suspended solid was collected by filtration, washed with water, and dried at 60° C. under vacuum. The solid was recrystallised from tert-butyl methyl ether to give 4'-[(2-ethylquinolin-4-yloxy)methyl]biphenyl-2-carbonitrile as a solid (1.9 g), m.p. 151°–153° C.; NMR(CDCl$_3$): 1.4(t, 3H), 2.97(q,2H), 5.35(s,2H), 6.76(s,1H), 7.4–7.6(m, 3H), 7.6–7.8(m, 6H), 8.0(d,1H), 8.25(d, 1H).

The starting material A was obtained as follows:—

(i) 2M Sodium carbonate solution (200 ml) was added to a stirred mixture of 4-methylphenylboronic acid (30 g), 2-bromobenzonitrile (36.4 g), palladium (II) chloride (0.4 g), methanol (200 ml) and toluene (200 ml) at 5° C. The temperature rose to approximately 20° C. and a solid precipitated. The reaction mixture was then heated at reflux for 2 hours. The reaction mixture was allowed to cool and water (100 ml) was added, followed by diatomaceous earth (5 g). The mixture was stirred for 15 minutes, then filtered through diatomaceous earth. The organic phase of the filtrate was separated and washed with 2M sodium carbonate solution and then water. The organic phase was then filtered and the filtrate evaporated. The resultant solid was recrystallised from petroleum ether (b.p. 110°–120° C.) to give 4'-methylbiphenyl-2-carbonitrile which was used without further purification.

(ii) A mixture of 4'-methylbiphenyl-2-carbonitrile (3.86 g), N-bromosuccinimide (3.92 g) and azo(-bisisobutyronitrile) (0.15 g) in chlorobenzene (75 ml) was heated at 70° C. for 3 hours. Further N-bromosuccinimide (0.3 g) and azo(bisisobutyronitrile) (0.05 g) was added and the mixture was heated for another 15 minutes. Heating was stopped and the mixture stirred for 16 hours at ambient temperature. Water (50 ml) was added and the mixture stirred for 30 minutes and filtered. The organic phase was separated, washed with water (50 ml) and dried (MgSO$_4$). The solvent was removed by evaporation and the resultant solid recrystallised from cyclohexane to give 4'-bromomethylbiphenyl-2-carbonitrile (3.9 g) (A) as a solid; NMR (CDCl$_3$): 4.55(s,2H), 7.4–7.85(m, 8H).

EXAMPLE 57

Using an analogous procedure to that described in Example 7, but starting from 6-(tert-butyloxycarbonyl-)aminomethyl-2-ethyl-4-([2'-(2-triphenylmethyl-2H-tetrazol-5-yl)biphenyl-4-yl]methoxy)quinoline, itself isolated as a foam [NMR: 1.40(t,3H), 1.45(s,9H), 2.96(q,2H), 4.37(d,2H), 4.83(brs,1H), 5.18(s,2H), 6.89–6.99(m,6H), 7.18–7.35(m,14H), 7.40–7.55(m,3H), 7.62(dd,1H), 7.92–8.02(m,3H); $^{13}$C NMR: (benzylic CH$_2$) 70.02] starting from 6-(tert-butyloxycarbonyl-)aminomethyl-2-ethyl-4-quinolone, there was thus obtained 6-aminomethyl-2-ethyl-4-[(2'-(1H-tetrazol-5-yl)biphenyl-4-yl)methoxy]quinoline dihydrochloride, m.p. 150°–153° C.; NMR (d$_6$-DMSO): 1.45(t,3H), 3.20(q,2H), 4.22–4.33(m,2H), 5.69(s,2H), 7.23(d,2H), 7.52–7.75(m,7H), 8.17(dd,1H), 8.34–8.46(m,2H), 8.62(brs,2H); mass spectrum (+ve FAB, DMSO/NBA): 437 (M+H)+; microanalysis, found: C,57.9; H,5.7; N,14.4; Cl,14.5; H$_2$O,3.7%; C$_{26}$H$_{24}$N$_6$O.2.25HCl.1.25H$_2$O.0.25(C$_2$H$_5$)$_2$O requires C,57.9; H,5.5; N,15.0; Cl,14.3; H$_2$O,4.0%.

6-(tert-butyloxycarbonyl)aminomethyl-2-ethyl-4-quinolone was obtained as follows:—

Cobalt (II) chloride (2.87 g) was added to a suspension of 2-ethyl-6-cyano-4-quinolone (1.2 g) in methanol (100 ml). Sodium borohydride (2.24 g) was added in small portions to the resulting purple suspension and the mixture stirred for 2 hours during which time a colloidal precipitate appeared. Excess borohydride was destroyed by careful acidification with 2M hydrochloric acid and the mixture was then made basic with 1M sodium hydroxide solution. Di-tert-butyl dicarbonate (1.32 g) was added to the resulting slurry and stirring was continued for 1 hour. The slurry was filtered through diatomaceous earth and washed with methanol (100 ml). The filtrate was evaporated and the residue was extracted with dichloromethane, dried (MgSO$_4$) and evaporated to give a cream foam. Trituration with diethyl ether gave 6-(tert-butyloxycarbonyl)aminomethyl-2-ethyl-4-quinolone (1.2 g) as a cream powder, m.p. 228° C. (dec.).

EXAMPLE 58

Using an analogous procedure to that described in Example 7, but starting from 4-[(2'-(2-triphenylmethyl-2H-tetrazol-5-yl)biphenyl-4-yl)methoxy]quinoline (A), there was obtained in 60% yield 4-[(2'-(1H-tetrazol-5-yl)biphenyl-4-yl)methoxy]quinoline hydrochloride, as a white solid, m.p. 162°–164° C.; NMR (d$_6$-DMSO): 5.7(s,2H), 7.2(d,2H), 7.45–7.8(complex m,7H), 7.9(t,1H), 8.1(dt,1H), 8.3(dt,2H), 9.2(dd,1H); mass spectrum (-ve FAB, DMSO/GLY): 378 (M-H)−; microanalysis, found: C,66.6; H,4.2; N,16.4%; C$_{23}$H$_{17}$N$_5$O.HCl requires: C,66.4; H,4.3; N,16.8%.

The starting material (A) was obtained as follows:—
(i) Powdered potassium acetate (17.5 g) was added to a solution of 5-[2-(4'-bromomethylbiphenylyl)]-2-triphenylmethyl-2H-tetrazole (50 g) (obtained as described in European Patent Application, Publication No. 0291969) and 1,4,7,10,13,16-hexaoxacyclooctadecane (100 mg) in 1,2-dimethoxyethane (DME) (600 ml), and the mixture was heated under reflux for 20 hours. Insoluble material was removed by filtration, and the residue triturated with a mixture of ethyl acetate and hexane (1:4 v/v) to give 5-[2-[4'-acetoxymethylbiphenylyl]-2-triphenylmethyl-2H-tetrazole (B) (41.8 g), as a cream powder, m.p. 119°–121° C.; NMR (CDCl$_3$): 2.1(s,3H), 5.0(s,2H), 6.8–6.95(complex m,8H), 7.2–7.55-(complex m,14H), 7.9–8.0(m,1H).
(ii) A solution of compound (B) (41.8 g) in tetrahydrofuran (THF) (200 ml) was added over a period of 40 minutes to a suspension of lithium borohydride (4.1 g) in THF (400 ml) stirred at 0° C. under an atmosphere of argon. The mixture was stirred at ambient temperature for 20 hours and then cooled to 0° C. 20% Aqueous citric acid solution (40 ml) was added and the mixture was diluted with saturated sodium chloride solution (600 ml). The mixture was extracted with ethyl acetate (2×500 ml) and the extracts were washed with water (500 ml) and saturated sodium chloride solution (500 ml). The extracts were dried (MgSO$_4$) and volatile material removed by evaporation. The residue was purified by flash chromatography, eluting with ethyl acetate/hexane (2:3 v/v), to give 5-[2-(4'-hydroxymethylbiphenylyl)]-2-triphenylmethyl-2H-tetrazole (C) (17.4 g), as a white solid, m.p. 168°–169° C. (after recrystallisation from a mixture of ethyl acetate and hexane (1:9 v/v)); NMR (CDCl$_3$): 4.6(s,2H), 6.85–7.0(m,6H), 7.2–7.5(complex m,16H), 7.9–8.0(m,1H).
(iii) Sodium hydride (60% dispersion in mineral oil; 80 mg) was added to a stirred solution of compound (C) (0.99 g) in DMF (10 ml). The mixture was stirred until evolution of hydrogen ceased and then 4-chloroquinoline (0.33 g) was added. The mixture was stirred for 24 hours, poured into water (100 ml) and extracted with ethyl acetate (2×50 ml). The extracts were washed with water (40 ml) and saturated sodium chloride solution (40 ml) and then dried (MgSO$_4$). Volatile material was removed by evaporation and the residue purified by flash chromatography, eluting with ethyl acetate/hexane (1:1 v/v), to give 4-[(2'-(2-triphenylmethyl-2H-tetrazol-5-yl)biphenyl-4-yl)methoxy]quinoline (A) (0.80 g), as a foam; NMR (CDCl$_3$): 5.2(s,2H), 6.8(d,1H), 6.85–6.95(m,6H), 7.15–7.55(complex m,17H), 7.7(t,1H), 7.95–8.25(m,3H), 8.7(d,1H).

EXAMPLE 59

Using an analogous procedure to that described in Example 7, but starting from 4-[(2-methoxy-2'-(2-triphenylmethyl-2H-tetrazol-5-yl)biphenyl-4-yl)methoxy]-2-methylquinoline (A), there was obtained 4-[(2-methoxy-2'-(1H-tetrazol-5-yl)biphenyl-4-yl)methoxy]-2-methylquinoline hydrochloride, as a white solid, m.p. 215°–218° C.; NMR (d$_6$-DMSO): 2.9(s,3H), 3.4(s,3H), 5.6(s,2H), 7.1(s,1H), 7.2–7.35(m,2H), 7.4–7.9(complex m,6H), 8.1(dt,1H), 8.25–8.35(m,2H); mass spectrum (-ve FAB, DMSO/GLY): 422 (M-H)−; microanalysis, found: C,65.3; H,4.7; N,14.9%; C$_{25}$H$_{20}$N$_5$O$_2$.HCl requires: C,65.3; H,4.8; N,15.2%.

The starting material (A) was obtained as follows:—
(i) A solution of 2-bromo-5-methylanisole (3.8 g) [obtained as described in J. Gen. Chem. U.S.S.R., 1932, 2, 455 (Chemical Abstracts, 1933, 27, 962)] in THF (50 ml) was added to magnesium turnings (0.47 g) and a catalytic amount of iodine under an atmosphere of argon. A catalytic volume of 1M methyl magnesium bromide in ether was added and the mixture was heated 50° C. for 1 hour, and then cooled to 0° C. Tributyltin chloride (5.6 g) was added dropwise over 5 minutes and the mixture was stirred for 18 hours. Volatile material was removed by evaporation and the residue partitioned between ether (50 ml) and saturated ammonium chloride solution (50 ml). The organic phase was separated and washed with saturated ammonium chloride solution (2×20 ml). The ether layer was separated, diluted with ethyl acetate (50 ml), and washed with water (25 ml), followed by saturated sodium chloride solution (50 ml). Volatile material was removed by evaporation and the residue purified by distillation to give (2-methoxy-4-methylphenyl)tributyl tin (B) (4.8 g), as an oil, b.p. 190° C. at 0.05 torr; NMR: 0.75–1.7 (complex m,27H), 2.4(s,3H), 3.8(s,3H), 6.6(t,1H), 6.8(d,1H), 7.2(d,1H).
(ii) A mixture of compound (B) (4.7 g), 2-bromobenzonitrile (1.8 g), tetrakis(triphenylphosphine)palladium (0.76 g) and azo(bisisobutyronitrile) (300 mg) in toluene (25 ml) was heated under reflux for 60 hours. The mixture was filtered through diatomaceous earth and the filtrate washed with water (25 ml) and dried (MgSO$_4$). Volatile material was removed by evaporation and the residue purified by flash chromatography, eluting with ethyl acetate/hexane (1:9 v/v), to give 2'-methoxy-4'-methylbiphenyl-2-carbonitrile (C) (0.78 g), as an oil; NMR: 2.4(s,3H), 3.85(s,3H), 6.8-6.9(m,2H), 7.2(d,1H), 7.3-7.5(m,2H), 7.55-7.75(m,2H).

(iii) A solution of compound (C) (0.78 g) and tributyltin azide (9.3 g) in toluene (20 ml) was heated under reflux for 48 hours. A 9M solution of hydrogen chloride in dioxan (10 ml) was added and volatile material was removed by evaporation. The residue was triturated with hexane to give 5-[2-(2'-methoxy-4'-methylbiphenylyl)]-2H-tetrazole (D) (0.65 g), as a solid which was used without purification; NMR (d$_6$-DMSO): 2.3(s,3H), 3.3(s,3H), 6.7(s,1H), 6.8(d,1H), 7.05(d,1H), 7.4-7.9(complex m,4H).

(iv) A solution of compound (D) (0.64 g), triphenylmethyl chloride (0.67 g) and triethylamine (0.46 g) in dichloromethane (5 ml) was left to stand for 3 hours. Dichloromethane (25 ml) was added, and the solution was washed with water (2×20 ml), saturated sodium chloride solution (20 ml), and then dried (MgSO$_4$). Volatile material was removed by evaporation and the residue triturated with hexane (50 ml). Recrystallisation from ethyl acetate gave 5-[2-(2'-methoxy-4'-methylbiphenylyl)]-2-triphenylmethyl-2H-tetrazole (E) (0.58 g), as a white solid, m.p. 180°-183° C.; NMR (d$_6$-DMSO): 2.3(s,3H), 3.3(s,3H), 6.6(s,1H), 6.7(d,1H), 6.7-6.9(m,6H), 6.95(d,1H), 7.3-7.6(complex m,12H), 7.9(dd,1H).

(v) A mixture of compound (E) (0.58 g), N-bromosuccinimide (0.20 g) and azo(bisisobutyronitrile) (18 mg) in carbon tetrachloride (10 ml) was heated under reflux for 3 hours. Insoluble material was removed by filtration and the filtrate concentrated. The residue was recrystallised from ethyl acetate/hexane to give 5-[2-(4'-bromomethyl-2'-methoxybiphenylyl)]-2-triphenylmethyl-2H-tetrazole (F) (0.58 g), as a white solid, m p. 182°-183° C.; NMR (d$_6$-DMSO): 3.3(s,1H), 4.6(s,2H), 6.7-6.9(complex m,8H), 6.95-7.05(m,1H), 7.25-7.6-(complex m,12H), 7.85-7.95(m,1H).

(vi) Using an analogous procedure to that described in Example 7, but starting from compound (F), there was obtained in 32% yield 4-[(2-methoxy-2'-(2-triphenylmethyl-2H-tetrazol-5-yl)biphenyl-4-yl)methoxy]-2-methylquinoline (A), as a foam; NMR d$_6$-DMSO): 2.6(s,3H), 3.4(s,3H), 5.3(s,2H), 6.8-7.2(complex m,10H), 7.3-7.5(complex m,11H), 7.5-8.0(m,6H).

EXAMPLE 60 (Note: all parts by weight)

The compounds of the invention may be administered for therapeutic or prophylactic use to warm-blooded animals such as man in the form of conventional pharmaceutical compositions, typical examples of which include the following:—

| | |
|---|---|
| a) Capsule (for oral administration) | |
| Active ingredient * | 20 |
| Lactose powder | 578.5 |
| Magnesium stearate | 1.5 |
| b) Tablet (for oral administration) | |
| Active ingredient * | 50 |
| Microcrystalline cellulose 400 | 47.5 |
| Starch (pregelatinised) | |
| Magnesium stearate | 2.5 |
| c) Injectable Solution (for intravenous administration) | |
| Active ingredient * | 0.05-1.0 |
| Propylene glycol | 5.0 |
| Polyethylene glycol (300) | 3.0-5.0 |
| Purified water | to 100% |
| d) Injectable Suspension (for intramuscular administration) | |
| Active ingredient * | 0.05-1.0 |
| Methylcellulose | 0.5 |
| Tween 80 | 0.05 |
| Benzyl alcohol | 0.9 |
| Benzalkonium chloride | 0.1 |
| Purified water | to 100% |

Note: the active ingredient * may typically be an Example described hereinbefore and will conveniently be present as a pharmaceutically acceptable acid-addition salt, such as the hydrochloride salt. Tablets and capsules formulations may be coated in conventional manner in order to modify or sustain dissolution of the active ingredient. Thus, for example, they may be coated with a conventional enterically digestible coating.

Scheme 1

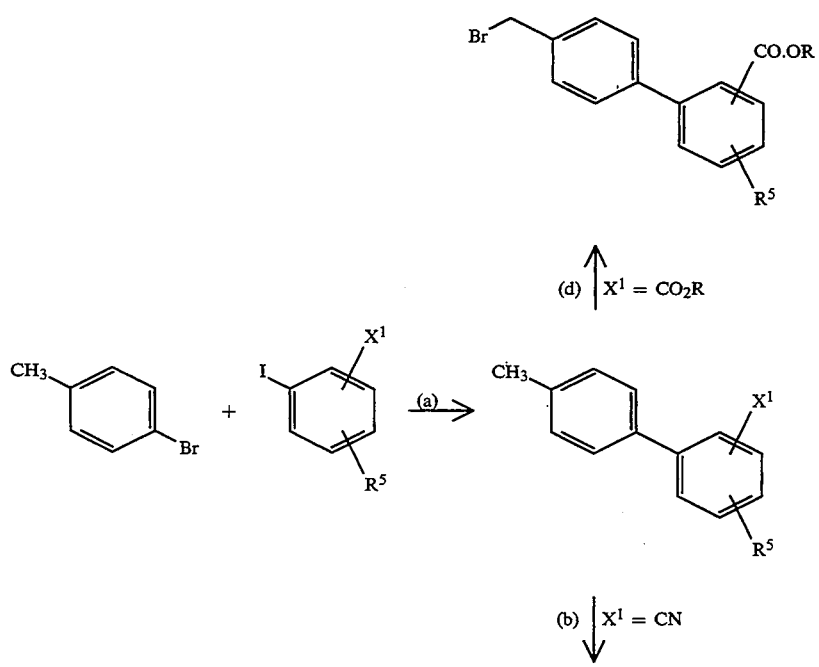

Scheme 1
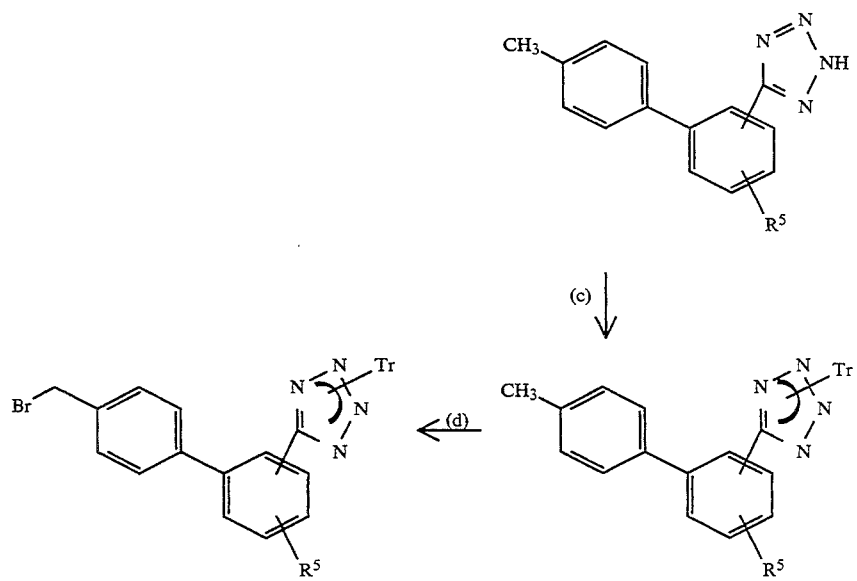
Note: R = lower alkyl, benzyl, phenyl; Tr = triphenylmethyl (trityl)
Reagents: a) BuLi/THF; ZnCl$_2$/Et$_2$O; Pd(Ph$_3$P)$_4$
b) Bu$_3$Sn.N$_3$/toluene; HCl/toluene
c) Tr.Cl/Et$_3$N/CH$_2$Cl$_2$
d) N-bromosuccinimide/azoisobutyronitrile/CCl$_4$
Chemical Formulae
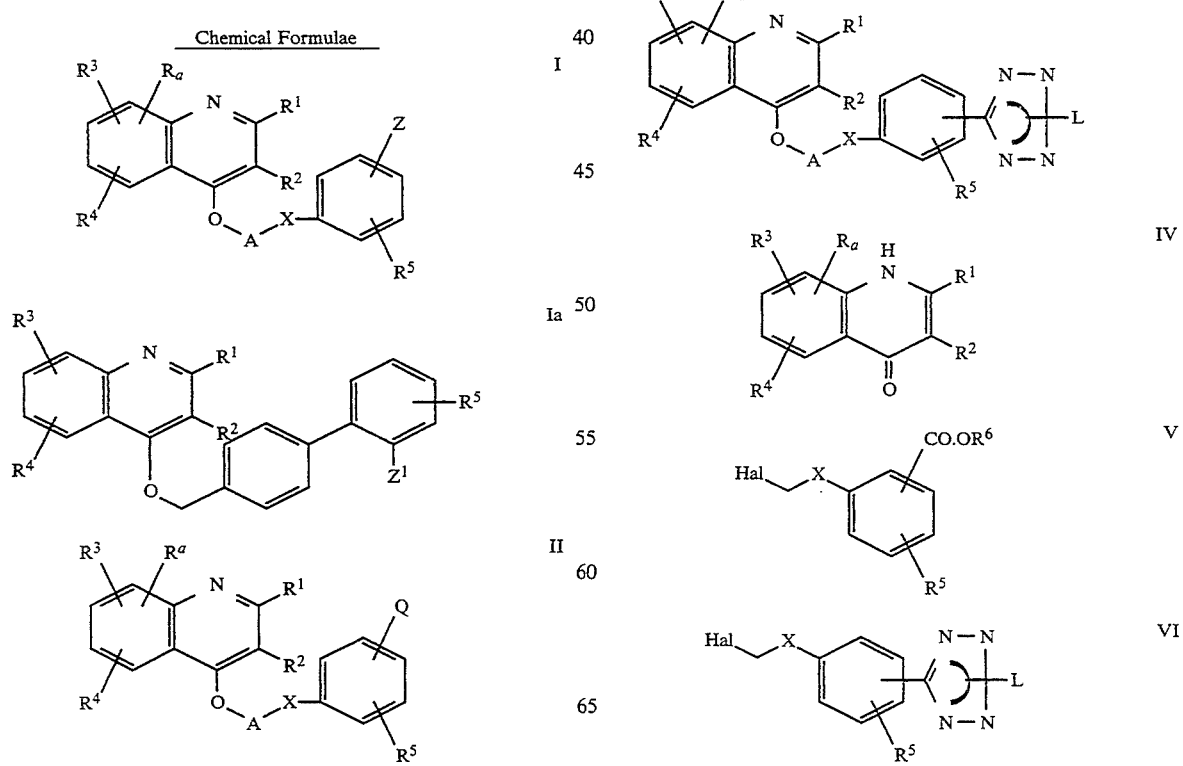

-continued
Chemical Formulae

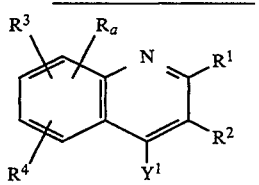
VII

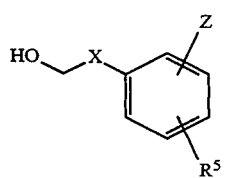
VIII

What we claim is:

1. A quinoline compound of the formula I

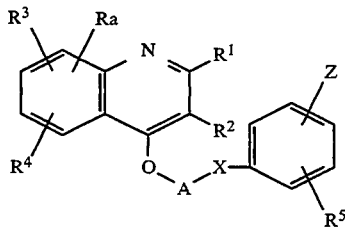
I wherein R¹ is hydrogen, (1-8C)alkyl, (3-8C)cycloalkyl, phenyl or substituted (1-4C) alkyl, the latter having one or more fluoro substituents or bearing a (3-8C)cycloalkyl, hydroxy, (1-4C)alkoxy or phenyl substituent; R² is hydrogen, methyl, ethyl, propyl, butyl, is0butyl, sec-butyl, pentyl or hexyl; R³ and R⁴ are independently selected from hydrogen (1-4C)alkyl, (1-4C)alkoxy, fluoro(1-4C)alkoxy, halogeno, hydroxy, trifluoromethyl, cyano, nitro, amino, (1-4C)alkanoylamino, alkylamino and dialkylamino of up to 6 carbon atoms, dialkylamino-alkyl of 3 to 8 carbon atoms, (1-4C)alkanoyl, carbamoyl, N-alkylcarbamoyl and di-(N-alkyl)carbamoyl of up to 7 carbon atoms, carboxy, (1-4C)alkoxycarbonyl, (1-6C)alkylthio, and substituted (1-4C)alkyl, the latter bearing an amino, hydroxy or (1-4C)alkoxy substituent; or R³ and R⁴ together form (1-4C)alkylenedioxy attached to adjacent carbon atoms of the benzene moiety of formula I; Ra and R⁵ are independently selected from hydrogen, (1-4C)alkyl, (1-4C)alkoxy, halogeno, trifluoromethyl, cyano and nitro; A is methylene; X is phenylene optionally bearing a substituent selected from (1-4C)alkyl, (1-4C)alkoxy, halogeno, trifluoromethyl, cyano and nitro Z is 1H-tetrazol-5-yl, —CO.NH.(1H-tetrazol-5-yl) or a group of the formula —CO.OR⁶ or —CO.NH.SO₂.R⁷ in which R⁶ is hydrogen or a non-toxic, biodegradable residue of a physiologically acceptable phenol, and R⁷ is (1-6C)alkyl, (3-8C)cycloalkyl or phenyl; and wherein any of said phenyl moieties may be unsubstituted or bear one or two substituents independently selected from (1-4C)alkyl, (1-4C)alkoxy, halogeno, cyano and trifluoromethyl; or a non-toxic salt thereof; but excluding methyl 2-((3-methoxycarbonylquinolin-4-yloxy)methyl) benzoate.

2. A compound as claimed in claim 1 wherein R¹ is hydrogen, methyl, ethyl, propyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, hydroxymethyl, 1-hydroxyethyl, 2-hydroxyethyl, cyclopropylmethyl, cyclopentylmethyl, cyclohexylmethyl, 2-methoxyethyl, 2-ethoxyethyl, benzyl, 1-phenylethyl, or 2-phenylethyl; R² is hydrogen, methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentyl-ethyl, carboxy, methoxycarbonyl, ethoxycarbonyl, propoxycarbonyl, cyano, nitro, phenyl, benzyl, 1-phenylethyl or 2-phenylethyl; R³ and R⁴ are independently selected from hydrogen, methyl, ethyl, methoxy, ethoxy, trifluoromethoxy, 2-fluoroethoxy, 2,2,2-trifluoroethoxy, 3,3,3-trifluoropropoxy, fluoro, chloro, bromo, iodo, hydroxy, trifluoromethyl, cyano, nitro, amino, formamido, acetamido, propanamido, methylamino, ethylamino, butylamino, dimethylamino, diethylamino, dipropylamino, dimethylaminomethyl, 2-(dimethylamino)ethyl, 2-(diethylamino)ethyl, 3-(diethylamino)propyl, formyl, acetyl, butyryl, carbamoyl, N-methylcarbamoyl, N-ethylcarbamoyl, N,N-dimethylcarbamoyl, N,N-diethylcarbamoyl, carboxy, methoxycarbonyl, ethoxycarbonyl, propoxycarbonyl, methylthio, ethylthio, butylthio, methylsulphinyl, ethylsulphinyl, butylsulphinyl, methylsulphonyl, ethylsulphonyl, butylsulphonyl, hydroxymethyl, 1-hydroxyethyl, 2-hydroxyethyl, aminomethyl, 2-aminoethyl, 2-methoxyethyl and 2-ethoxyethyl; or R³ and R⁴ together form methylenedioxy or ethylenedioxy attached to adjacent carbon atoms of the benzene moiety of formula I; Ra and R⁵ are independently selected from hydrogen, methyl, ethyl, methoxy, ethoxy, fluoro, chloro, bromo, iodo, trifluoromethyl, cyano and nitro; X is phenylene optionally bearing a substituent selected from methyl, ethyl, methoxy, ethoxy, fluoro, chloro, bromo, iodo, trifluoromethyl, cyano and nitro, R⁶ is hydrogen or a residue derived from a phenol or glycerol; and R⁷ is methyl, ethyl, propyl, isopropyl, butyl, pentyl, cyclobutyl, cyclopentyl, cyclohexyl or phenyl; and wherein any of said phenyl moieties may be unsubstituted or bear one or two substituents independently selected from methyl, ethyl, methoxy, ethoxy, fluoro, chloro, bromo, cyano and trifluoromethyl.

3. A compound as claimed in claim 1 wherein R¹ is hydrogen, (1-8C)alkyl, (3-8C)cycloalkyl, (3-8C)cycloalkyl-(1-4C)alkyl, phenyl or phenyl(1-4C)alkyl; R³, R⁴ and R⁵ are independently selected from hydrogen, (1-4C)alkyl, (1-4C)alkoxy, halogeno, trifluoromethyl, cyano and nitro; and Ra is hydrogen.

4. A compound as claimed in claim 1 wherein R³ and R⁴ are independently selected from hydrogen, (1-4C)alkyl, (1-4C)alkoxy, fluoro(1-4C)alkoxy, halogeno, trifluoromethyl, cyano, nitro, amino, (1-4C)alkanoylamino, alkylamino and dialkylamino of up to 6 carbon atoms, dialkylamino-alkyl of 3 to 8 carbon atoms, (1-4C)alkanoyl, carbamoyl, N-alkylcarbamoyl and di-(N-alkyl)carbamoyl of up to 7 carbon atoms, carboxy, (1-4C)alkoxycarbonyl, (1-6C)alkylthio, (1-6C)alkylsulphinyl, (1-6C)alkylsulphonyl, and substituted (1-4C)alkyl, the latter bearing an amino, hydroxy or (1-4C)alkoxy substituent; or R³ and R⁴ together form (1-4C)alkylenedioxy attached to adjacent carbon atoms of the benzene moiety of formula I; and Ra is hydrogen.

5. A compound as claimed in claim 1 wherein the quinoline moiety together with the attached substituents R¹, R², R³ and R⁴, and Ra when present, is selected from 2-methylquinoline, 2-ethylquinoline, 2-ethyl-6- methoxyquinoline, 6,7-dimethoxy-2-ethylquinoline, 2-ethyl-5,6,7-trimethoxyquinoline, 2-ethyl-6-hydroxyquinoline, 2-ethyl-6-methylthioquinoline, 2-ethyl-7-hydroxymethylquinoline, 2-ethyl-6-(2-fluoroethoxy)quinoline, 2-ethyl-6-(2,2,2-trifluoroethoxy)quinoline, 2-ethyl-6-carboxamidoquinoline, 2-ethyl-6-fluoroquinoline, 2-ethyl-6-isopropoxyquinoline and 6-aminomethyl-2-ethylquinoline.

6. A compound as claimed in claim 1 selected from:—
2-methyl-4-[(2'-(1H-tetrazol-5-yl)biphenyl-4-yl)methoxy]quinoline;
2-ethyl-4-[(2'-(1H-tetrazol-5-yl)biphenyl-4-yl)methoxy]quinoline;
6,8-dimethyl-2-ethyl-4-[(2'-(1H-tetrazol-5-yl)biphenyl-4-yl)methoxy]quinoline;
2-ethyl-6-methylthio-4-[(2'-(1H-tetrazol-5-yl)biphenyl-4-yl)methoxy]quinoline;
2-ethyl-7-hydroxymethyl-4-[(2'-(1H-tetrazol-5-yl)biphenyl-4-yl)methoxy]quinoline;
2-ethyl-6-(2-fluoroethoxy)-4-[(2'-(1H-tetrazol-5-yl)biphenyl-4-yl)methoxy]quinoline;
2-ethyl-6-(2,2,2-trifluoroethoxy)-4-[(2'-(1H-tetrazol-5-yl)biphenyl-4-yl)methoxy]quinoline;
6-carboxamido-2-ethyl-4-[(2'-(1H-tetrazol-5-yl)-biphenyl-4-yl)methoxy]quinoline;
6-cyano-2-ethyl-4-[(2'-(1H-tetrazol-5-yl)biphenyl-4-yl)methoxy]quinoline;
2-ethyl-6-fluoro-4-[(2'-(1H-tetrazol-5-yl)biphenyl-4-yl)methoxy]quinoline;
2-ethyl-6-isopropoxy-4-[(2'-(1H-tetrazol-5-yl)biphenyl-4-yl)methoxy]quinoline; and
6-aminomethyl-2-ethyl-4-[(2'-(1H-tetrazol-5-yl)biphenyl-4-yl)methoxy]quinoline;
and the non-toxic salts thereof.

7. A compound as claimed in claim 1 selected from:—
2-methyl-4-[(2'-(1H-tetrazol-5-yl)biphenyl-4-yl)methoxy]quinoline;
2-ethyl-4-[(2'-(1H-tetrazol-5-yl)biphenyl-4-yl)methoxy]quinoline; and
2-ethyl-6-isopropoxy-4-[(2'-(1H-tetrazol-5-yl)biphenyl-4-yl)methoxy]quinoline; and the non-toxic salts thereof.

8. A salt as claimed in claim 1 which is selected from salts with acids forming physiologically acceptable anions and, for those compounds of formula I which are acidic, alkali metal, alkaline earth metal, aluminium and ammonium salts, and salts with organic bases affording physiologically acceptable anions.

9. A method for treating hypertension in a warm-blooded animal requiring such treatment which comprises administering to said animal a pharmaceutically effective amount of a compound of formula I, or a non-toxic salt thereof, as defined in claim 1.

10. A pharmaceutical composition which comprises a compound of the formula I, or a non-toxic salt thereof, as claimed in claim 1, together with a pharmaceutically acceptable diluent or carrier.

11. A compound of the formula II

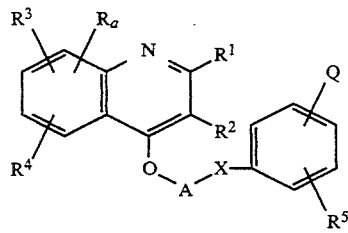

wherein $R^1$ is hydrogen, (1–8C)alkyl, (3–8C)cycloalkyl, phenyl or substituted (1–4C)alkyl, the latter having one or more fluoro substituents or bearing a (3–8C)cycloalkyl, hydroxy, (1–4C)alkoxy or phenyl substituent; $R^2$ is hydrogen, methyl, ethyl, propyl, butyl, isobutyl, sec-butyl, pentyl or hexyl; $R^3$ and $R^4$ are independently selected from hydrogen (1–4C)alkyl, (1–4C)alkoxy, fluoro(1–4C)alkoxy, halogeno, hydroxy, trifluoromethyl, cyano, nitro, amino, (1–4C)alkanoylamino, alkylamino and dialkylamino of up to 6 carbon atoms, dialkylamino-alkyl of 3 to 8 carbon atoms, (1–4C)alkanoyl, carbamoyl, N-alkylcarbamoyl and di-(N-alkyl)carbamoyl of up to 7 carbon atoms, carboxy, (1–4C)alkoxycarbonyl, (1–6C)alkylthio, and substituted (1–4C)alkyl, the latter bearing an amino, hydroxy or (1–4C)alkoxy substituent; or $R^3$ and $R^4$ together form (1–4C)alkylenedioxy attached to adjacent carbon atoms of the benzene moiety of formula I; Ra and $R^5$ are independently selected from hydrogen, (1–4C)alkyl, (1–4C)alkoxy, halogeno, trifluoromethyl, cyano and nitro; A is methylene; X is phenylene optionally bearing a substituent selected from (1–4C)alkyl, (1–4C)alkoxy, halogeno, trifluoromethyl, cyano and nitro and wherein any of said phenyl moieties may be unsubstituted or bear one or two substituents independently selected from (1–4C)alkyl, (1– 4C)alkoxy, halogeno, cyano and trifluoromethyl; or a non-toxic salt thereof; but excluding methyl 2-((3-methoxycarbonylquinolin-4-yloxy)-methyl) benzoate, and Q is a protected carboxy group selected from phenoxycarbonyl, benzylcarbonyl and carbamoyl.

12. A compound of the formula III

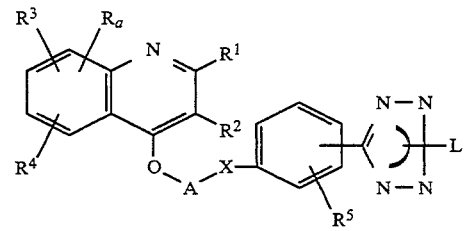

wherein $R^1$ is hydrogen, (1–8C)alkyl, (3–8C) cycloalkyl, phenyl or substituted (1–4C) alkyl, the latter having one or more fluoro substituents or bearing a (3–8C)cycloalkyl, hydroxy, (1–4C)alkoxy or phenyl substituent; $R^2$ is hydrogen, methyl, ethyl, propyl, butyl, isobutyl, sec-butyl, pentyl or hexyl; $R^3$ and $R^4$ are independently selected from hydrogen (1–4C)alkyl, (1–4C)alkoxy, fluoro(1–4C)alkoxy, halogeno, hydroxy, trifluoromethyl, cyano, nitro, amino, (1–4C)alkanoylamino, alkylamino and dialkylamino of up to 6 carbon atoms, dialkylamino-alkyl of 3 to 8 carbon atoms, (1–4C)alkanoyl, carbamoyl, N-alkylcarbamoyl and di-(N-alkyl)carbamoyl of up to 7 carbon atoms, carboxy, (1–4C)alkoxycarbonyl, (1–6C)alkylthio, and substituted (1–4C)alkyl, the latter bearing an amino, hydroxy or (1–4C)alkoxy substituent; or $R^3$ and $R^4$ together form (1–4C)alkylenedioxy attached to adjacent carbon atoms of the benzene moiety of formula I; Ra and $R^5$ are independently selected from hydrogen, (1–4C)alkyl, (1–4C)alkoxy, halogeno, trifluoromethyl, cyano and nitro; A is methylene; X is phenylene optionally bearing a substituent selected from (1–4C)alkyl, (1–4C)alkoxy, halogeno, trifluoromethyl, cyano and nitro, and wherein any of said phenyl moieties may be unsubstituted or bear one or two substituents independently selected from (1–4

C)alkyl, (1–4C) alkoxy, halogeno, cyano and trifluoromethyl; or a non-toxic salt thereof; but excluding methyl 2-((3-methoxycarbonylquinolin-4-yloxy)methyl) benzoate, and L is trityl or benzhydryl.

13. A quinoline compound of the formula Ia

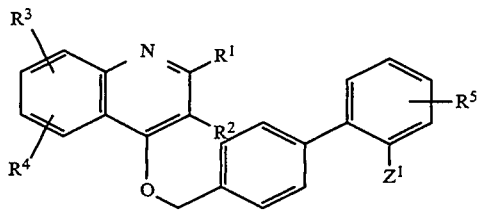

wherein R¹ is hydrogen, (1–8C)alkyl, (3–8C)cycloalkyl, phenyl or substituted (1–4C)alkyl, the latter having one or more fluoro substituents or bearing a (3–8C)cycloalkyl, hydroxy, (1–4C)alkoxy or phenyl substituent; R² is hydrogen, methyl, ethyl, propyl, butyl, isobutyl, sec-butyl, pentyl or hexyl; R³ and R⁴ are independently selected from hydrogen, (1–4C) alkyl, (1–4C)alkoxy, fluoro(1–4C)alkoxy, halogeno, hydroxy, trifluoromethyl, cyano, nitro, amino, (1–4C)alkanoylamino, alkylamino and dialkylamino of up to 6 carbon atoms, dialkylamino-alkyl of 3 to 8 carbon atoms, (1–4C)alkanoyl, carbamoyl, N-alkylcarbamoyl and di-(N-alkyl)carbamoyl of up to 7 carbon atoms, carboxy, (1–4C) alkoxycarbonyl, (1–6C)alkylthio, and substituted (1–4C) alkyl, the latter bearing an amino hydroxy or (1–4C)alkoxy substituent; or R³ and R⁴ together form (1–4C)alkylenedioxy attached to adjacent carbon atoms of the benzene moiety of formula Ia; R⁵ is selected from hydrogen, (1–4C)alkyl, (1–4C)alkoxy, halogeno, trifluoromethyl, cyano and nitro; Z¹ is carboxy or 1H-tetrazol-5-yl; and wherein any of said phenyl moieties may be unsubstituted or bear one or two substituents independently selected from (1–4C) alkyl, (1–4C)alkoxy, halogeno, cyano and trifluoromethyl; or a non-toxic salt thereof.

14. A compound as claimed in claim 13 wherein R¹ is hydrogen, methyl, ethyl, propyl, butyl, isobutyl, sec-butyl, pentyl, hexyl, cyclopropyl, cyclopentyl, cyclohexyl, phenyl, fluoromethyl, trifluoromethyl, 2,2,2-trifluoroethyl, pentafluoroethyl, hydroxymethyl, 1-hydroxyethyl, 2-hydroxyethyl, cyclopropylmethyl, cyclopentylmethyl, cyclohexylmethyl, 2-methoxyethyl, 2-ethoxyethyl, benzyl, 1-phenylethyl, or 2-phenylethyl; R² is hydrogen, methyl, ethyl, propyl, butyl, isobutyl, sec-butyl, pentyl, hexyl, cyclopropyl, cyclopentyl, cyclohexyl, cyclopropylmethyl, cyclopentylmethyl, cyclohexylmethyl, 2-cyclopentyl-ethyl, carboxy, methoxycarbonyl, ethoxycarbonyl, propoxycarbonyl, cyano, nitro, phenyl, benzyl, 1-phenylethyl or 2-phenylethyl; R³ and R⁴ are independently selected from hydrogen, methyl, ethyl, methoxy, ethoxy, trifluoromethoxy, 2-fluoroethoxy, 2,2,2-trifluoroethoxy, 3,3,3-trifluoropropoxy, fluoro, chloro, bromo, iodo, hydroxy, trifluoromethyl, cyano, nitro, amino, formamido, acetamido, propanamido, methylamino, ethylamino, butylamino, dimethylamino, diethylamino, dipropylamino, dimethylaminomethyl, 2-(dimethylamino)ethyl, 2-(diethylamino)ethyl, 3-(diethylamino)propyl, formyl, acetyl, butyryl, carbamoyl, N-methylcarbamoyl, N-ethylcarbamoyl, N,N-dimethylcarbamoyl, N,N-diethylcarbamoyl, carboxy, methoxycarbonyl, ethoxycarbonyl, propoxycarbonyl, methylthio, ethylthio, butylthio, methylsulphinyl, ethylsulphinyl, butylsulphinyl, methylsulphonyl, ethylsulphonyl, butylsulphonyl, hydroxymethyl, 1-hydroxyethyl, 2-hydroxyethyl, aminomethyl, 2-aminoethyl, 2-methoxyethyl and 2-ethoxyethyl; or R³ and R⁴ together form methylenedioxy or ethylenedioxy attached to adjacent carbon atoms of the benzene moiety of formula Ia; R⁵ is selected from hydrogen, methyl, ethyl, methoxy, ethoxy, fluoro, chloro, bromo, iodo, trifluoromethyl, cyano and nitro; and wherein any of said phenyl moieties may be unsubstituted or bear one or two substituents independently selected from methyl, ethyl, methoxy, ethoxy, fluoro, chloro, bromo, cyano and trifluoromethyl.

15. A compound as claimed in claim 13 wherein R¹ is hydrogen, (1–8C)alkyl, (3–8C)cycloalkyl, (3–8C)cycloalkyl-(1–4C)alkyl, phenyl or phenyl(1–4C)alkyl; and R³, R⁴ and R⁵ are independently selected from hydrogen (1–4C)alkyl, (1–4C)alkoxy, halogeno, trifluoromethyl, cyano and nitro.

16. A compound as claimed in claim 13 wherein R³ and R⁴ are independently selected from hydrogen, (1–4C)alkyl, (1–4C)alkoxy, fluoro(1–4C)alkoxy, halogeno, trifluoromethyl, cyano, nitro, amino, (1–4C)alkanoylamino, alkylamino and dialkylamino of up to 6 carbon atoms, dialkylamino-alkyl of 3 to 8 carbon atoms, (1–4C)alkanoyl, carbamoyl, N-alkylcarbamoyl and di-(N-alkyl)carbamoyl of up to 7 carbon atoms, carboxy, (1–4C)alkoxycarbonyl, (1–6C)alkylthio, (1–6C)alkylsulphinyl, (1–6C)alkylsulphonyl, and substituted (1–4C)alkyl, the latter bearing an amino, hydroxy or (1–4C)alkoxy substituent; or R³ and R⁴ together form (1–4C)alkylenedioxy attached to adjacent carbon atoms of the benzene moiety of formula Ia.

17. A compound as claimed in claim 13 wherein the quinoline moiety together with the attached substituents R¹, R², R³ and R⁴, is selected from 2-methylquinoline, 2-ethylquinoline, 2-ethyl-6-methoxyquinoline, 6,7-dimethoxy-2-ethylquinoline, 2-ethyl-6-hydroxyquinoline, 2-ethyl-6-methylthioquinoline, 2-ethyl-7-hydroxymethylquinoline, 2-ethyl-6-(2-fluoroethoxy)quinoline, 2-ethyl-6-(2,2,2-trifluoroethoxy)quinoline, 2-ethyl-6-carboxamidoquinoline, 2-ethyl-6-fluoroquinoline, 2-ethyl-6-isopropoxyquinoline and 6-aminomethyl-2-ethylquinoline.

18. A salt as claimed in claim 13 which is selected from salts with acids forming physiologically acceptable anions and, for those compounds of formula I which are acidic, alkali metal, alkaline earth metal, aluminium and ammonium salts, and salts with organic bases affording physiologically acceptable anions.

19. A method for treating hypertension in a warm-blooded animal requiring such treatment which comprises administering to said animal a pharmaceutically effective amount of a compound of formula Ia, or a non-toxic salt thereof, as defined in claim 13.

20. A pharmaceutical composition which comprises a compound of the formula Ia, or a non-toxic salt thereof, as claimed in claim 13, together with a pharmaceutically acceptable diluent or carrier.

21. A compound of the formula II

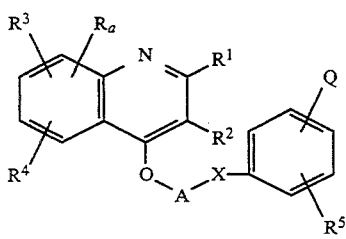 II wherein $R^1$ is hydrogen, (1–8C)alkyl, (3–8C)cycloalkyl, phenyl or substituted (1–4C)alkyl, the latter having one or more fluoro substituents or bearing a (3–8C)cycloalkyl, hydroxy, (1–4C)alkoxy or phenyl substituent; $R^2$ is hydrogen, methyl, ethyl, propyl, butyl, isobutyl, sec-butyl, pentyl or hexyl; $R^3$ and $R^4$ are independently selected from hydrogen, (1–4C)alkyl, (1–4C)alkoxy, fluoro(1–4C)alkoxy, halogeno, hydroxy, trifluoromethyl, cyano, nitro, amino, (1–4C)alkanoylamino, alkylamino and dialkylamino of up to 6 carbon atoms, dialkylamino-alkyl of 3 to 8 carbon atoms, (1–4C)alkanoyl, carbamoyl, N-alkylcarbamoyl and di-(N-alkyl)carbamoyl of up to 7 carbon atoms, carboxy, (1–4C)alkoxycarbonyl, (1–6C)alkylthio, and substituted (1–4C)alkyl, the latter bearing an amino hydroxy or (1–4C)alkoxy substituent; or $R^3$ and $R^4$ together form (1–4C)alkylenedioxy attached to adjacent carbon atoms of the benzene moiety of formula Ia; $R^5$ is selected from hydrogen, (1–4C)alkyl, (1–4C)alkoxy, halogeno, trifluormethyl, cyano and nitro; or a non-toxic salt thereof, Ra is hydrogen, A is methylene, X is p-phenylene and Q is a protected carboxy group selected from phenoxycarbonyl, benzyloxycarbonyl and carbamoyl.

22. A compound of the formula III

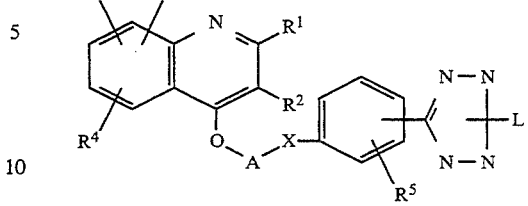 III wherein $R^1$ is hydrogen, (1–8C)alkyl, (3–8C)cycloalkyl, phenyl or substituted (1–4C)alkyl, the latter having one or more fluoro substituents or bearing a (3–8C)cycloalkyl, hydroxy, (1–4C)alkoxy or phenyl substituent; $R^2$ is hydrogen, methyl, ethyl, propyl, butyl, isobutyl, sec-butyl, pentyl or hexyl; $R^3$ and $R^4$ are independently selected from hydrogen, (1–4C)alkyl, (1–4C)alkoxy, fluoro(1–4C)alkoxy, halogeno, hydroxy, trifluoromethyl, cyano, nitro, amino, (1–4C)alkanoylamino, alkylamino and dialkylamino of up to 6 carbon atoms, dialkylamino-alkyl of 3 to 8 carbon atoms, (1–4C)alkanoyl, carbamoyl, N-alkylcarbamoyl and di-(N-alkyl)carbamoyl of up to 7 carbon atoms, carboxy, (1–4C)alkoxycarbonyl, (1–6C)alkylthio, and substituted (1–4C)alkyl, the latter bearing an amino hydroxy or (1–4C)alkoxy substituent; or $R^3$ and $R^4$ together form (1–4C)alkylenedioxy attached to adjacent carbon atoms of the benzene moiety of formula Is; $R^5$ is selected from hydrogen, (1–4C)alkyl, (1–4C)alkoxy, halogeno, trifluormethyl, cyano and nitro; or a non-toxic salt thereof, Ra is hydrogen, A is methylene, X is p-phenylene and L is trityl or benzhydryl.

* * * * *